(12) United States Patent
Omori

(10) Patent No.: US 8,998,797 B2
(45) Date of Patent: Apr. 7, 2015

(54) SURGICAL SYSTEM

(75) Inventor: Shigeru Omori, Ashigarakami-gun (JP)

(73) Assignee: Karl Storz GmbH & Co. KG (DE)

( * ) Notice: Subject to any disclaimer, the term of this patent is extended or adjusted under 35 U.S.C. 154(b) by 1339 days.

(21) Appl. No.: 12/175,520

(22) Filed: Jul. 18, 2008

(65) Prior Publication Data

US 2009/0192519 A1 Jul. 30, 2009

(30) Foreign Application Priority Data

Jan. 29, 2008 (JP) ................................. 2008-017707

(51) Int. Cl.
    *A61B 1/00* (2006.01)
    *B25J 19/00* (2006.01)
    *G06F 19/00* (2011.01)
    *A61B 19/00* (2006.01)

(52) U.S. Cl.
    CPC .......... *A61B 19/2203* (2013.01); *A61B 19/5212* (2013.01); *A61B 19/56* (2013.01); *A61B 2019/2223* (2013.01); *A61B 2019/5276* (2013.01); *A61B 2019/5291* (2013.01); *Y10S 901/15* (2013.01); *Y10S 901/16* (2013.01)

(58) Field of Classification Search
    USPC ............ 600/118, 424–425; 606/130; 700/245
    See application file for complete search history.

(56) References Cited

U.S. PATENT DOCUMENTS

| | | | | |
|---|---|---|---|---|
| 5,368,015 A | * | 11/1994 | Wilk .............................. | 600/104 |
| 5,572,999 A | * | 11/1996 | Funda et al. ................... | 600/118 |
| 5,876,325 A | * | 3/1999 | Mizuno et al. ................. | 600/102 |
| 6,120,433 A | * | 9/2000 | Mizuno et al. ................. | 600/102 |
| 6,331,181 B1 | * | 12/2001 | Tierney et al. ................. | 606/130 |
| 6,529,765 B1 | * | 3/2003 | Franck et al. .................. | 600/427 |
| 6,889,116 B2 | | 5/2005 | Jinno | |
| 6,968,224 B2 | * | 11/2005 | Kessman et al. ............... | 600/407 |
| 2001/0051881 A1 | * | 12/2001 | Filler ................................ | 705/3 |
| 2003/0011624 A1 | * | 1/2003 | Ellis ............................. | 345/646 |

(Continued)

FOREIGN PATENT DOCUMENTS

| | | |
|---|---|---|
| JP | 2001-61860 A | 3/2001 |
| JP | 2002-102248 | 4/2002 |

(Continued)

OTHER PUBLICATIONS

Stoll et al., Ultrasound-based Servoing of Manipulators for Telesurgery, Oct. 28, 2001, [Retrieve on Dec. 18, 2012], Retrieve from the internet: http://www.biorobotics.harvard.edu/pubs/2001/SPIE01_US.pdf, 8 pages.*

(Continued)

*Primary Examiner* — John P Leubecker
*Assistant Examiner* — Arnaldo Torres Diaz
(74) *Attorney, Agent, or Firm* — St. Onge Steward Johnston & Reens LLC

(57) ABSTRACT

A surgical system performs a surgical procedure on a patient with manipulators and an endoscope. The surgical system has a display unit for simultaneously displaying a plurality of items of information including an endoscopic image captured by the endoscope, and a wireless image processor for transmitting information to the display unit and processing the plurality of items of information to be displayed by the display unit. The information about the endoscopic image is transmitted from the endoscope to the wireless image processor through a link including at least a portion based on wireless communications.

11 Claims, 17 Drawing Sheets

(56) References Cited

U.S. PATENT DOCUMENTS

| | | | |
|---|---|---|---|
| 2004/0111183 A1* | 6/2004 | Sutherland et al. | 700/245 |
| 2005/0033117 A1* | 2/2005 | Ozaki et al. | 600/109 |
| 2006/0142657 A1* | 6/2006 | Quaid et al. | 600/424 |
| 2006/0149418 A1* | 7/2006 | Anvari | 700/245 |
| 2006/0229594 A1* | 10/2006 | Francischelli et al. | 606/27 |
| 2006/0259193 A1* | 11/2006 | Wang et al. | 700/245 |
| 2007/0021738 A1* | 1/2007 | Hasser et al. | 606/1 |
| 2007/0276234 A1* | 11/2007 | Shahidi | 600/437 |

FOREIGN PATENT DOCUMENTS

| | | |
|---|---|---|
| JP | 2003-61969 | 3/2003 |
| JP | 2005-296259 A | 10/2005 |

OTHER PUBLICATIONS

Office Action issued Aug. 21, 2012 in Japanese Patent Application No. 2008-017707 (with partial English-language translation).

\* cited by examiner

SURGICAL SYSTEM

BACKGROUND OF THE INVENTION

1. Field of the Invention

The present invention relates to a surgical system for performing a desired surgical procedure on a patient with at least manipulators and an internal image capturing means.

2. Description of the Related Art

According to a laparoscopic surgical operation process, small holes are opened in the abdominal region, for example, of a patient, and an endoscope, e.g., a hard mirror, and manipulators or forceps, are inserted into such holes. The surgeon performs a surgical operation on the patient with the manipulators or forceps, while watching an image captured by the endoscope and displayed on a display monitor. Since the laparoscopic surgical operation process does not require a laparotomy to be performed, and the operation is less burdensome on the patient and greatly reduces the number of days required for the patient to spend in the hospital before recovering from the operation and being released from the hospital. Therefore, the range of surgical operations in which the endoscopic surgical operation process may be applied is expected to increase.

As disclosed in Japanese Laid-Open Patent Publication No. 2002-102248 and Japanese Laid-Open Patent Publication No. 2003-061969, a manipulator system comprises a manipulator and a controller for controlling the manipulator. The manipulator comprises an operating unit which is manually operated, and a working unit replaceably mounted on the operating unit.

The working unit comprises a long joint shaft and a distal-end working unit (also referred to as an "end effector") mounted on the distal end of the joint shaft. The operating unit has motors for actuating the working unit through wires. The wires have proximal end portions wound around respective pulleys. The controller energizes the motors of the operating unit to cause the pulleys to move the wires circulatively.

There has also been proposed a surgical system (medical robot system) for actuating medical manipulators with robot arms (see, for example, U.S. Pat. No. 6,331,181). The medical robot system can be remotely controlled by a master arm, and can be moved in various ways under a programmed control.

The medical robot system has the robot arms, which can selectively be used depending on the surgical technique required. One of the robot arms incorporates an endoscope therein for capturing an image representing the inside of a body cavity, which is capable of being visually confirmed on a display monitor.

In order for the surgeons to decide on treatments properly and quickly in laparoscopic surgical operation processes, it is desirable that the surgeons should be able to see internal images obtained by an internal image capturing means such as an endoscope, images of the operating states of the manipulators, and diagnostic images captured by various diagnostic devices.

In the operating room, the surgical operation on a patient is attended by a plurality of people including not only the surgeons who actually operate on the patient, but also nurses and operators and technicians who handle various devices and instruments. During the surgery, it is desirable for those staff members to be able to move freely out of physical interference with the devices, instruments, and wires and cables, and also to be able to share up-to-date information about the surgical operation in progress.

SUMMARY OF THE INVENTION

It is an object of the present invention to provide a surgical system which allows the surgeons to recognize internal images obtained by an internal image capturing means and information about various devices and instruments used and various diagnostic images, and also allows the surgeons and other staff members to move freely in an operating room equipped with various devices and instruments for thereby performing surgical operations properly and quickly.

According to one aspect of the present invention, there is provided a surgical system for performing a surgical procedure on a patient, comprising a manipulator for performing a surgical operation on the patient, internal image capturing means for capturing an internal image of the patient, display means for simultaneously displaying a plurality of items of information including the internal image captured by the internal image capturing means, and information processing means for transmitting information to the display means and processing the plurality of items of information to be displayed by the display means, wherein the information about the internal image is transmitted from the internal image capturing means to the information processing means through a link including at least a portion based on wireless communications.

The display means can display the internal image captured by the internal image capturing means, which may be an endoscope, an MRI system, or an ultrasonic diagnostic device, simultaneously with information about other devices and instruments. The surgeon can appropriately recognize the current status of a surgical operation being performed on the patient by seeing the simultaneously displayed items of information, and make judgements with respect to surgical treatments on the patient. Since the transmission of the information between the display means and the internal image capturing means and the like through a link including at least a portion based on wireless communications, wires and cables in the operating room are greatly reduced, allowing staff members to move easily in the operating room. The display means can even display image information from a device which is used only temporarily during the surgery and system data thereof, at the same time as the internal image without the need for wires and cables in the operating room, for the surgeon to treat the patient appropriately.

The surgical system may further comprise a medical robot system including a robot arm for moving the manipulator, the manipulator being mounted on the robot arm, operating means for operating the manipulator and the robot arm, and operation control means for controlling operation of the manipulator and the robot arm based on an input signal from the operating means. Though the surgical system with the medical robot system tends to employ more wires and cables than ordinary manual surgical systems, the number of wires and cables used is relatively small because of the link including wireless communications.

Operational information representing operating states of the manipulator and the robot arm may be transmitted from the operation control means to the information processing means through a link including at least a portion based on wireless communications, and the display means may display the operational information simultaneously with the internal image.

The surgical system may further comprise a data server for storing information about an affected-region image captured in advance of an affected region of the patient. The information about the affected-region image may be transmitted from the data server to the information processing means through a link including at least a portion based on wireless communications, and the display means may display the affected-region image simultaneously with the internal image.

The surgical system may further comprise ultrasonic diagnostic means for acquiring an ultrasonic image of the affected region of the patient. Information about the ultrasonic image may be transmitted from the ultrasonic diagnostic means to the information processing means through a link including at least a portion based on wireless communications, and the display means may display the ultrasonic image simultaneously with the internal image.

Even if the display means displays various information including images from various devices and instruments, since the information is transmitted to the display means by way of wireless communications, wires and cables in the operating room are not many and disorganized. The display means can even display image information from a device which is used only temporarily during the surgery, such as the ultrasonic diagnostic means, at the same time as the internal image without the need for wires and cables in the operating room, for the surgeon to treat the patient appropriately. In addition, it is easy to move in the operating room to make the temporarily used device ready for use.

The operation control means may read the information about the affected-region image stored in the data server, set positional coordinates of the affected region in the affected-region image, and guide movement of the manipulator to the affected region based on the positional coordinates. The information processing means or the operation control means may process positional information of the affected region based on the positional coordinates in correlation to the information about the internal image. The display means may display the positional information of the affected region in superposed relation to the internal image.

The surgical system may further comprise an operation switch for selecting and switching between the plurality of items of information displayed by the display means. The operation switch may be provided as a touch-panel switch on a display screen of the display means or provided on the display means or the information processing means. Then, the information on the display means can be changed easily.

The information processing means may include a multi-window processor for setting and editing a plurality of windows on the display means for displaying the plurality of items of information on the display means simultaneously and promptly.

The information processing means may include bypass display means for processing the information about the internal image and displaying the internal image on the display means by bypassing the multi-window processor. The surgical system with the bypass display means operates as a duplexed system for continuously performing a surgical operation in the even of an unexpected failure.

The surgical system makes it possible to perform a surgical process for performing a surgical procedure on a patient with at least the manipulator and the internal image capturing means, wherein information about the internal image is transmitted from the internal image capturing means to the information processing means through a link including at least a portion based on wireless communications, and the plurality of items of information including the internal image are simultaneously displayed by the display means. The manipulator may be mounted on the movable robot arm, and the manipulator and the robot arm may be operated by the operating means.

According to another aspect of the present invention, since the display means is capable of displaying the internal image captured by the internal image capturing means simultaneously with information about other devices and instruments, the surgeon or the like can appropriately recognize the current statue of a surgical operation being performed on the patient by seeing the simultaneously displayed items of information, and appropriately make judgements with respect to surgical treatments on the patient.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
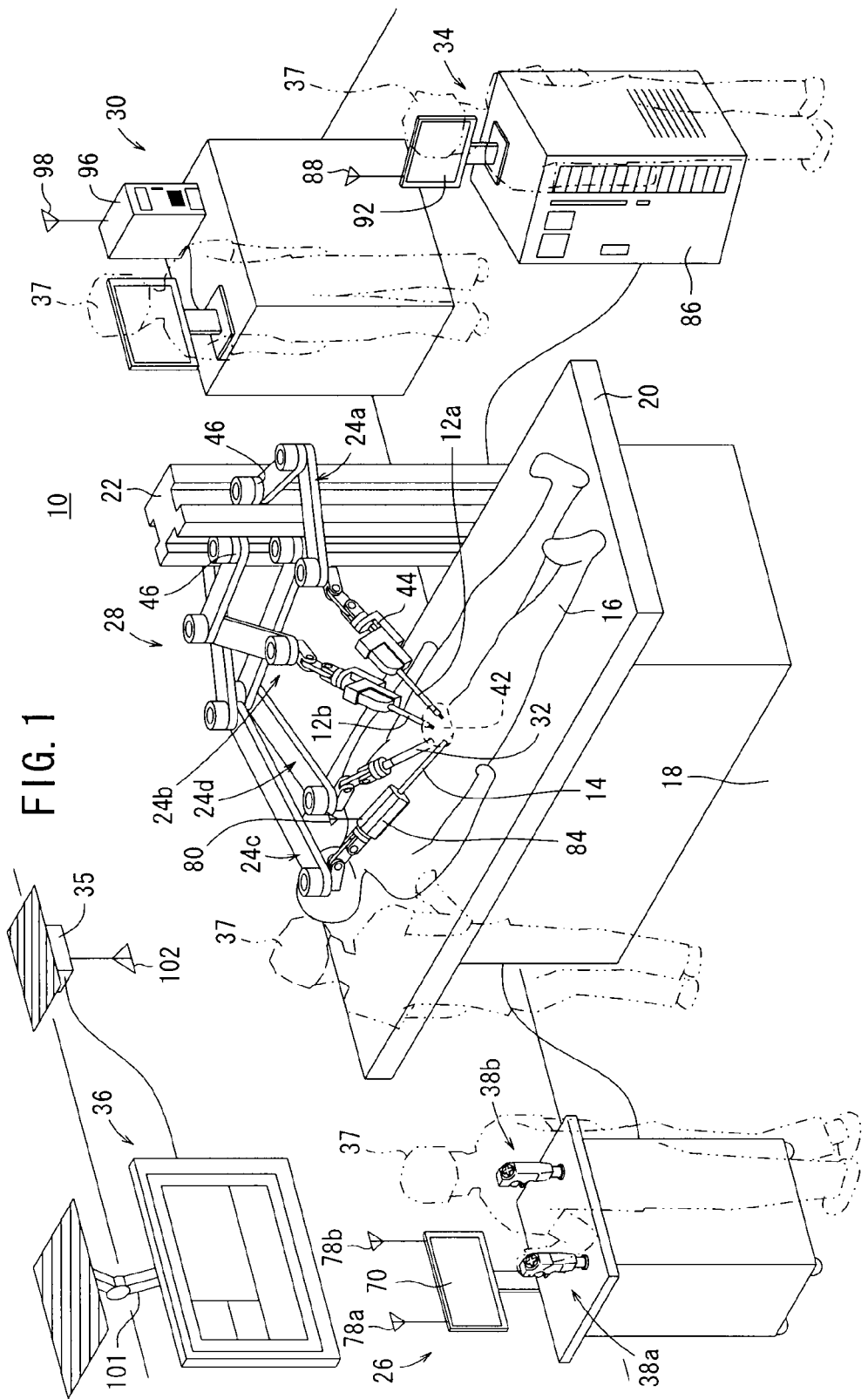
FIG. 1 is a perspective view of an operating room incorporating a surgical system according to an embodiment of the present invention.

Like or corresponding parts shall be denoted by like or corresponding reference characters throughout the views.

Surgical systems according to preferred embodiments of the present invention will be described below with reference to the drawings.

As shown in FIG. 1, a surgical system 10 according to an embodiment of the present invention performs a surgical operation, e.g., a laparoscopic operation, on a patient 16 using manipulators 12a, 12b, an endoscope 14 as an internal image capturing means, etc.

The surgical system 10 comprises a surgical robot 28 including a station 22 in the form of a vertical column disposed near a surgical bed 20 disposed in an operating room 18, four robot arms 24a, 24b, 24c, 24d mounted on the station 22, and a console (operation control means) 26 for controlling the surgical robot 28 in its entirety. The surgical system 10 also comprises a data server 30 for storing information such as X-ray CT and MRI diagnostic images (affected-region images) which have been captured of an affected image of the patient 16, an ultrasonic diagnostic device (ultrasonic diagnostic means) 34 for acquiring an ultrasonic image with a probe (ultrasonic diagnostic probe) 32 mounted on the distal end of the robot arm 24d, and a display unit (display means) 36 for simultaneously displaying an endoscopic image acquired by the endoscope 14 and an ultrasonic image acquired by the ultrasonic diagnostic device 34. The surgical system 10 serves as a medical robot system for performing a surgical operation on the patient 16 by actuating the robot arms 24a through 24d.

A wireless image processor (information processing means, access point) 35 is disposed, for example, near the center of or centrally on the ceiling of the operating room 18. The wireless image processor 35 is supplied with various signals by way of wireless communications, which represent an endoscopic image of the patient 16 acquired by the endoscope 14 and output from the endoscope 14, operational information about an operating state of the surgical robot 28 which is output from the console 26, X-ray CT and MRI diagnostic images (affected-region images) output from the data server 30, and an echo image (ultrasonic image) generated from a signal from the probe 32 by and output from the ultrasonic diagnostic device 34. The images and operational information based on the signals supplied to the wireless image processor 35 are displayed on the display unit 36. The images and operational information displayed on the display unit 36 can be shared by all of staff members 37 including surgeons, nurses, technicians, etc. who attend the surgical operation using the surgical system 10 in the operating room 18. At least part of the transmission of the signals in the surgical system 10 may be carried out by way of wireless communications. The signals may be transmitted to each other from antennas (access points) that are connected to the various devices by wires.

The console 26 can exchange information with the robot arms 24a through 24d through communication means such as wired communication means, wireless communication means, a network, or a combination thereof. The console 26 does not need to control the surgical robot 28 in its entirety, but the robot arms 24a through 24d may be feedback-controlled by their own controllers. The robot arms 24a and 24b may be actuated under the control of the console 26 for being operated according to automatic programmed operations or may be manually actuated by respective joysticks (operating means) 38a, 38b provided on the console 26. The robot arms 24a and 24b also may be actuated through a combination of automatic programmed operations and manually controlled operations.

Figure 2:
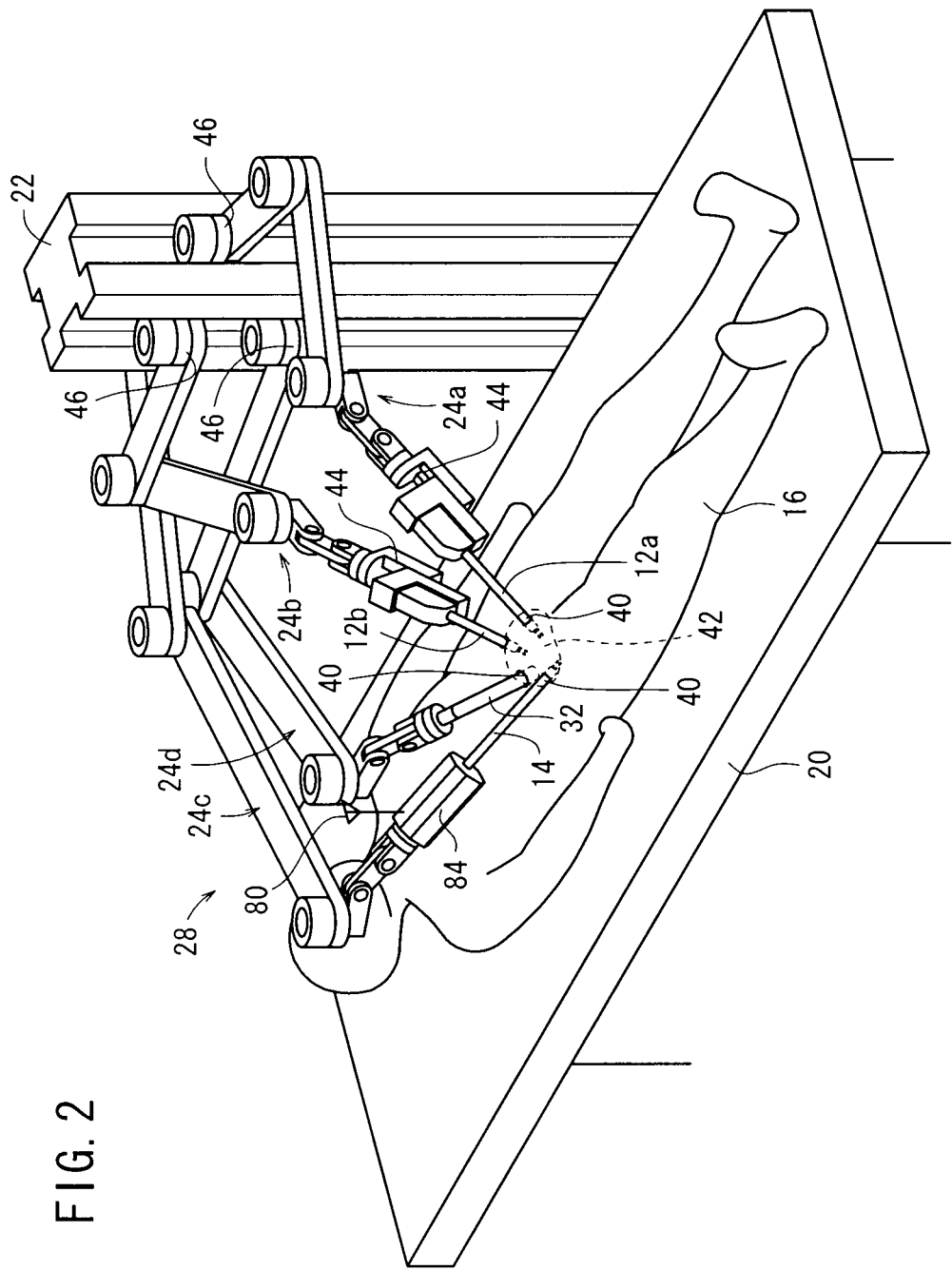
FIG. 2 is an enlarged perspective view of a surgical robot of the surgical system shown in FIG. 1.

As shown in FIG. 2, the robot arms 24a, 24b have the manipulators 12a, 12b respectively on their distal ends. The robot arm 24c has the endoscope 14 on its distal end, and the robot arm 24d has the probe 32 on its distal end. The manipulators 12a, 12b, the endoscope 14, and the probe 32 are inserted into a body cavity 42 of the patient 16 through respective trocars 40. The station 22 may comprise a plurality of stations supporting the respective robot arms 24a through 24d. The manipulators 12a, 12b, the endoscope 14, and the probe 32 are removably mounted on the respective robot arms 24d through 24d.

Each of the robot arms 24a through 24d has an articulated mechanism, e.g., a mechanism with independent six axes. The robot arms 24a through 24d are controlled by the console 26 to set the manipulators 12a, 12b, the endoscope 14, and the probe 32 to arbitrary postures at arbitrary positions within the operating ranges of the robot arms 24a through 24d. The robot arms 24a, 24b have respective slide mechanisms 44 for moving the manipulators 12a, 12b back and forth along the axes of the distal ends thereof, and respective lifting and lowering mechanisms 46 vertically movable along the station 22. The robot arms 24c, 24d may also have slide mechanisms 44 for moving the endoscope 14 and the probe 32 in the same manner as the manipulators 12a, 12b. The robot arms 24a through 24d may be structurally identical to each other, or may be of different structures depending on the types of the manipulators 12a, 12b, the endoscope 14, and the probe 32.

The manipulators 12a, 12b mounted respectively on the robot arms 24a, 24b serve to perform direct surgical techniques on an affected region of the patient 16. A gripper and scissors, for example, are mounted respectively as distal-end working units of the manipulators 12a, 12b. Alternatively, a retractor may be mounted for retracting an organ or the like within a body cavity 42 to a given place to allow the surgeon to have a wider operative field, as the distal-end working unit of one of the manipulators 12a, 12b.

Structural details of the manipulators 12a, 12b and joints between the manipulators 12a, 12b and the robot arms 24a, 24b will be described below.

Figure 3:
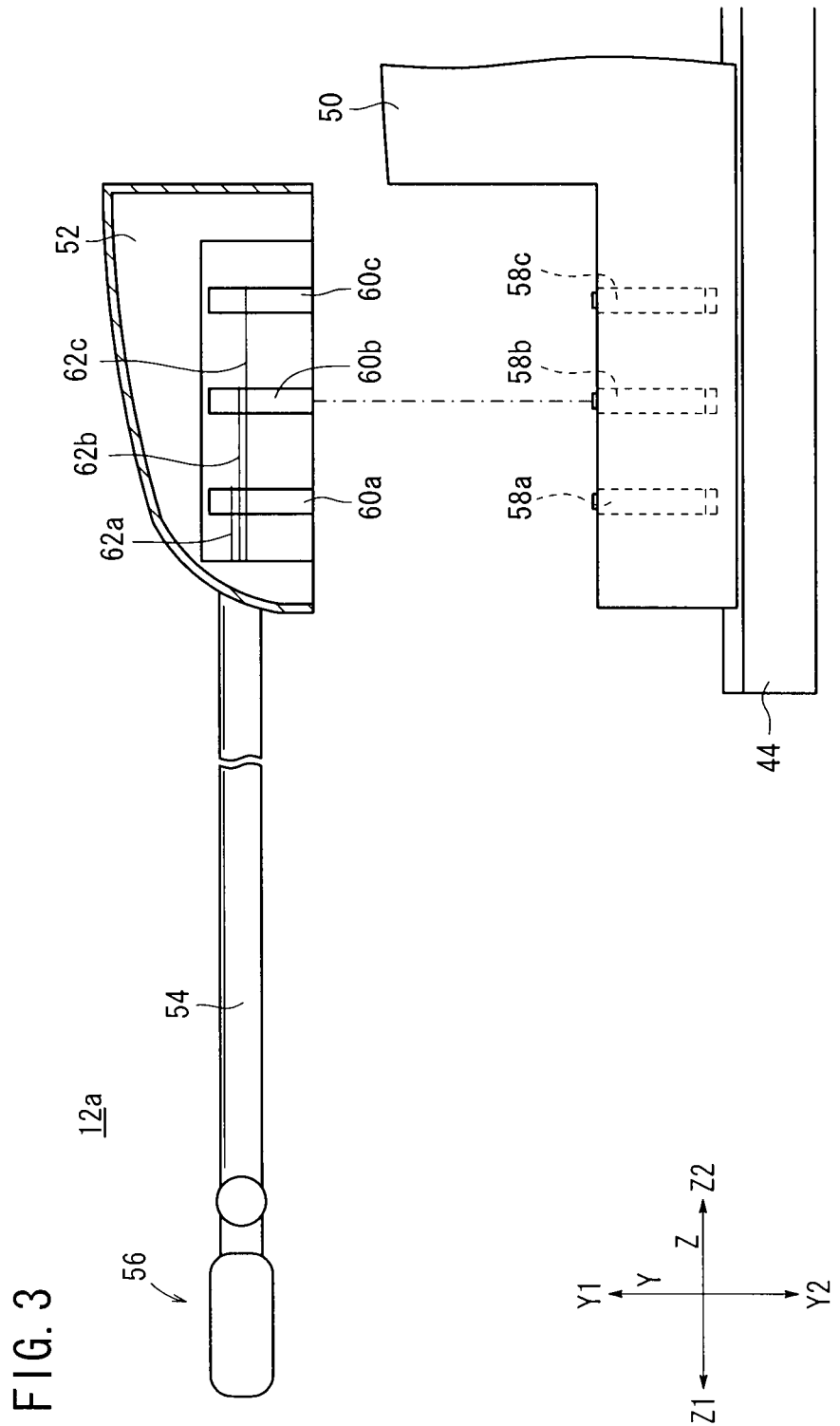
FIG. 3 is a side elevational view, partly in cross section, of a manipulator of the surgical robot.
Figure 4:
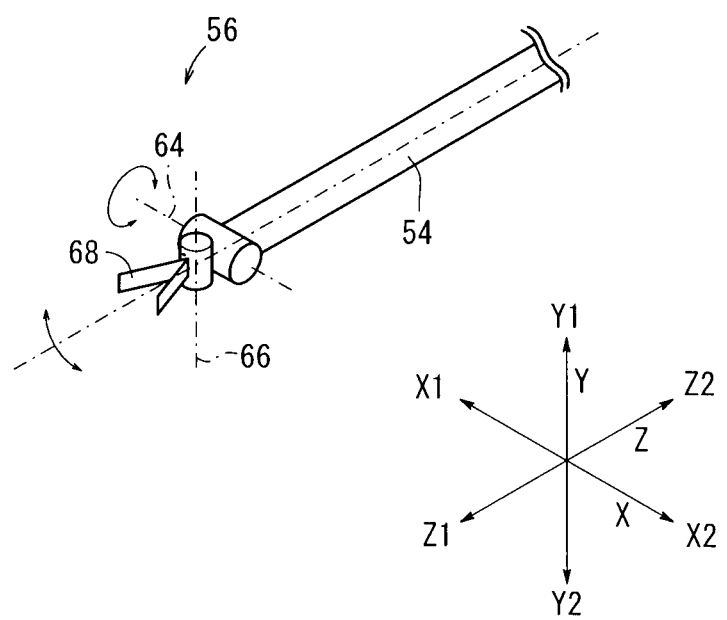
FIG. 4 is a perspective view of a distal-end working unit.

As shown in FIGS. 3 and 4, it is assumed that directions established with respect to the manipulator 12a include X directions representing horizontal transverse directions of the manipulator 12a, Y directions representing vertical transverse directions of the manipulator 12a, and Z directions representing longitudinal directions of the manipulator 12a, i.e., a joint shaft 54 thereof. The X directions include an X1 direction representing a rightward direction as viewed from the front of the manipulator 12a and an X2 direction representing a leftward direction as viewed from the front of the manipulator 12a. The Y directions include a Y1 direction representing an upward direction and a Y2 direction representing a downward direction. The Z directions include a Z1 direction representing a forward direction and a Z2 direction representing a rearward direction. Since the manipulators 12a, 12b are substantially identical in structure to each other in the present embodiment, only structural details of the manipulator 12a and a joint between the manipulator 12a and the robot arm 24a will be described below.

As shown in FIG. 3, the manipulator 12a is removably mounted on a slider 50 that is disposed on the distal end of the robot arm 24a. The slider 50 is made slidable in the Z directions on the robot arm 24a by the slide mechanism 44. The slider 50 supports three motors 58a, 58b, 58c mounted therein in an array along the Z directions.

The manipulator 12a comprises a connecting block 52 for connection to the slider 50, a hollow joint shaft 54 extending from the connecting block 52 in the Z1 direction, and a distal-end working unit 56 mounted on the distal end of the joint shaft 54.

The connecting block 52 is removably and replaceably mounted on the slider 50 by a removable mount mechanism. The connecting block 52 supports pulleys 60a, 60b, 60c mounted thereon in an array along the Z directions and held in engagement with the respective motors 58a, 58b, 58c. The motors 58a, 58b, 58c or the pulleys 60a, 60b, 60c have noncircular teeth and the pulleys 60a, 60b, 60c or the motors 58a, 58b, 58c have noncircular recesses. The noncircular teeth engage in the respective noncircular recesses for transmitting rotation of the motors 58a, 58b, 58c to the pulleys 60a, 60b, 60c.

Wires 62a, 62b, 62c are trained respectively around the pulleys 60a, 60b, 60c. The wires 62a, 62b, 62c are flexible and annular in shape, wherein portions thereof are fixed to the pulleys 60a, 60b, 60c for preventing slippage on the pulleys 60a, 60b, 60c. The wires 62a, 62b, 62c are trained, e.g., in 1.5 turns around the pulleys 60a, 60b, 60c, and extend in the Z1 direction in the joint shaft 54. When the pulleys 60a, 60b, 60c are rotated about their own axes by the motors 58a, 58b, 58c, one of the two turns of each of the wires 62a, 62b, 62c is wound around the pulley, and the other turn is paid out from the pulley. The wires 62a, 62b, 62c are spaced from each other in the Y directions so as to be held out of interference with each other.

The joint shaft 54 extends in the Z1 direction from the connecting block 52, and the distal-end working unit 56 is mounted on the distal end of the joint shaft 54. The joint shaft 54 may have a joint, not shown, somewhere along its length, so that the distal-end working unit 56 can effectively be operated as a retractor in the body cavity 42 according to a surgical technique for pushing a desired organ in the body cavity 42 while being kept out of physical interference with the other manipulator 12c and other organs.

As shown in FIG. 4, the distal-end working unit 56 is mounted on the distal end of the joint shaft 54, and comprises a pulley (rotor) around which the wire 62a is wound, a pulley around which the wire 62b is wound, and a pulley around which the wire 62c is wound. When the wires 62a, 62b, 62c are moved back and forth upon rotation of the pulleys 60a, 60b, 60c in the connecting block 52, the pulleys in the distal-end working unit 56 are driven to rotate, causing the distal-end working unit 56 to move about three axes. The motions of the distal-end working unit 56 include tilting motions about a pitch axis (joint) 64 and a yaw axis (joint) 66 and opening and closing motions of a gripper 68, for example. In addition to the tilting motions or instead of the tilting motions, the distal-end working unit 56 may be rotated about a roll axis extending along the axis of the joint shaft 54. The gripper 68 comprises a pair of gripper arms, one or both of which are openable. The distal-end working unit 56 may be of the same mechanism as the distal-end working unit of the medical manipulator disclosed in Japanese Laid-Open Patent Publication No. 2003-061969, for example.

Since the pitch axis 64, the yaw axis 66, and the gripper 68 can possibly cause a mutual interference, the console 26 calculates an amount of interference and controls the wires 62a, 62b, 62c to move back and forth to compensate for an interfering movement. In other words, the console 26 controls the wires 62a, 62b, 62c such that when it moves one of the movable members, it prevents the other from moving into interference with the moved one.

Figure 5:
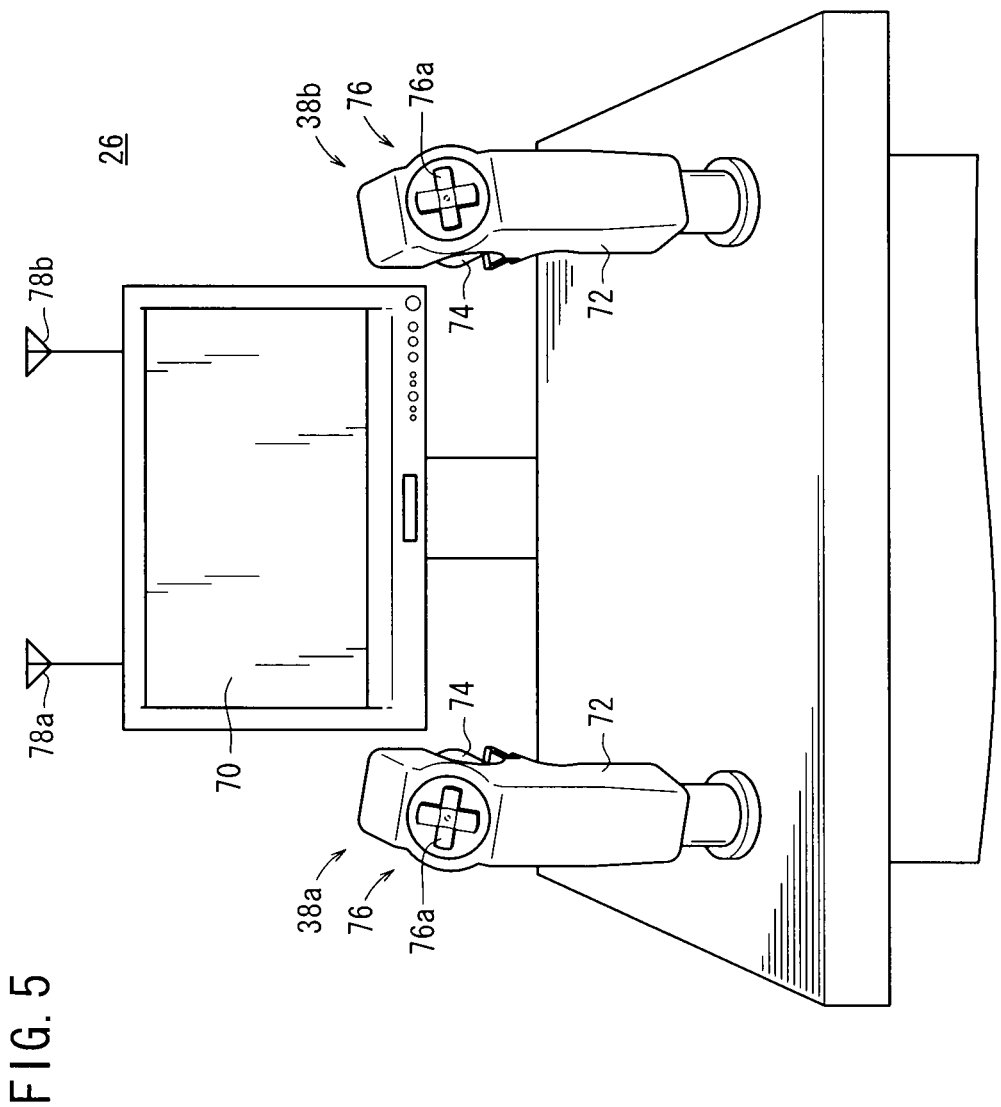
FIG. 5 is a perspective view of a console.

As shown in FIG. 5, the console 26 has two joysticks 38a, 38b as manually operating means (operating units), and a display monitor 70. The display monitor 70 displays an image captured by the endoscope 14 and information representing an operating state of the surgical robot 28. The display monitor 70 may be dispensed with because the surgical system 10 has the display unit 36.

The robot arms 24a, 24b can individually be operated by the joysticks 38a, 38b. The robot arms 24c, 24d can also be operated by another input means, not shown. For the robot arms 24c, 24d, the joysticks 38a, 38b may selectively be used, or a similar joystick or joysticks may be added to the console 26. The joysticks 38a, 38b are positioned at respective left and right positions where they can easily be operated by the user. The joysticks 38a, 38b may be replaced with a master arm.

The joysticks 38a, 38b are vertically movable, twistable, and tiltable in all directions for moving the robot arms 24a, 24b to make corresponding motions. When the joysticks 38a, 38b are released from the hands of the user, they automatically return to their upright orientations shown in FIG. 5. The joysticks 38a, 38b are basically identical in construction to each other, and have a handle grip 72 that is mainly gripped by a human hand, a trigger lever 74 that is pushed and pulled by an index finger and a middle finger, and a composite input pad 76 that is mainly gripped by a thumb. When the trigger lever 74 is operated, the gripper 68 is opened and closed. The composite input pad 76 includes a central criss-cross see-saw switch 76a. When the see-saw switch 76a is operated, the distal-end working unit 56 is tilted about the pitch axis 64 and the yaw axis 66.

The console 26 further includes a transceiver 78 (see FIG. 7) connected to an antenna 78a for transmitting and receiving information to and from the wireless image processor 35 by way of wireless communications and an antenna 78b for transmitting and receiving image data (ultrasonic image information) and control signals to and from the ultrasonic diagnostic device 34 by way of wireless communications, and a controller 79 for controlling the wireless communications or the like.

Figure 7:
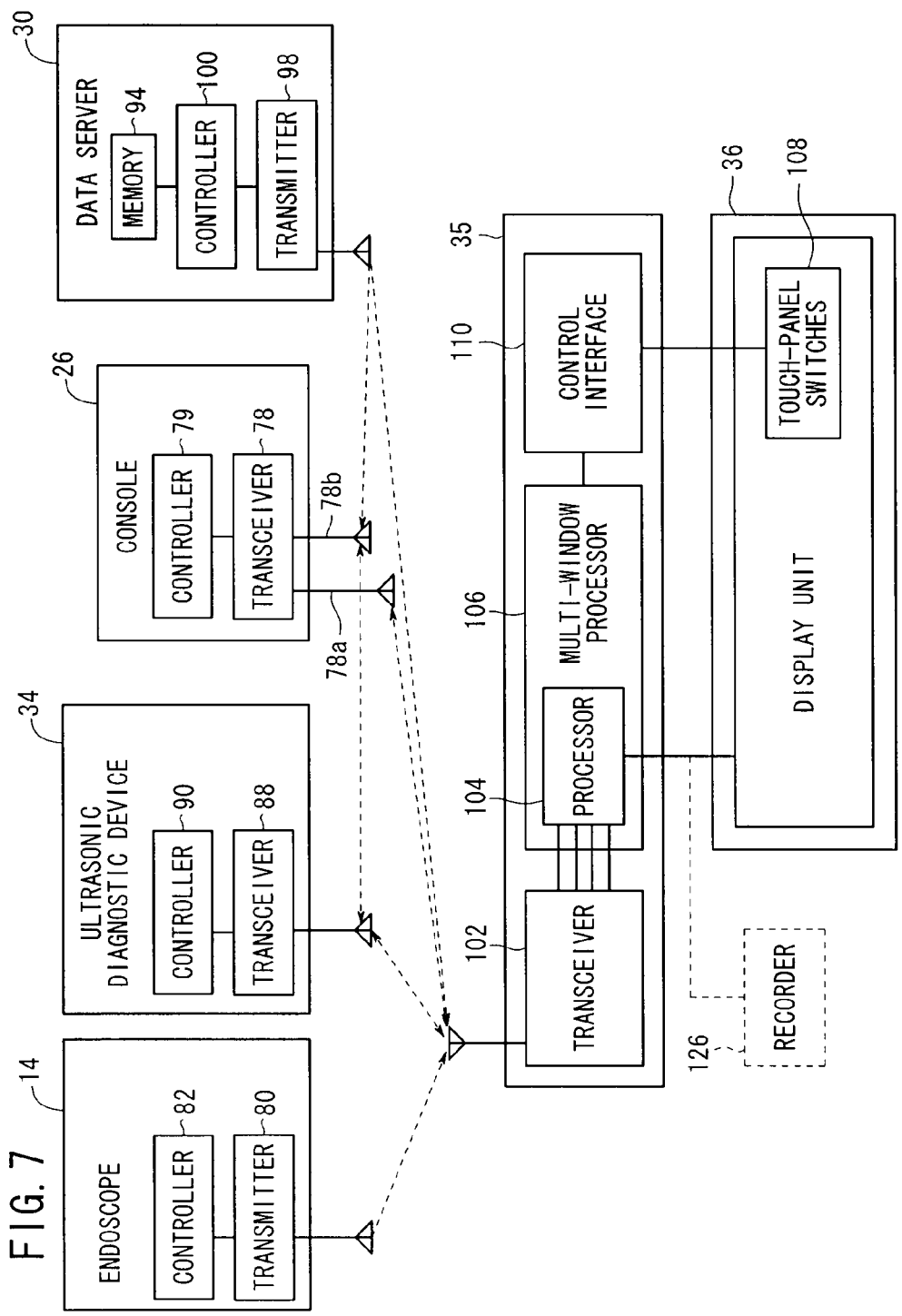
FIG. 7 is a block diagram of a circuit arrangement of the surgical system according to the embodiment of the present invention.

As shown in FIG. 7, the endoscope 14 comprises a transmitter 80 connected to an antenna for transmitting information about an acquired endoscopic image to the wireless image processor 35 by way of wireless communications, and a controller (endoscope control means) 82 for controlling the wireless communications or the like. The transmitter 80 and the controller 82 are housed in a housing 84 (FIG. 2) on the proximal end of the endoscope 14 which is connected to the robot arm 24c.

Figure 9:
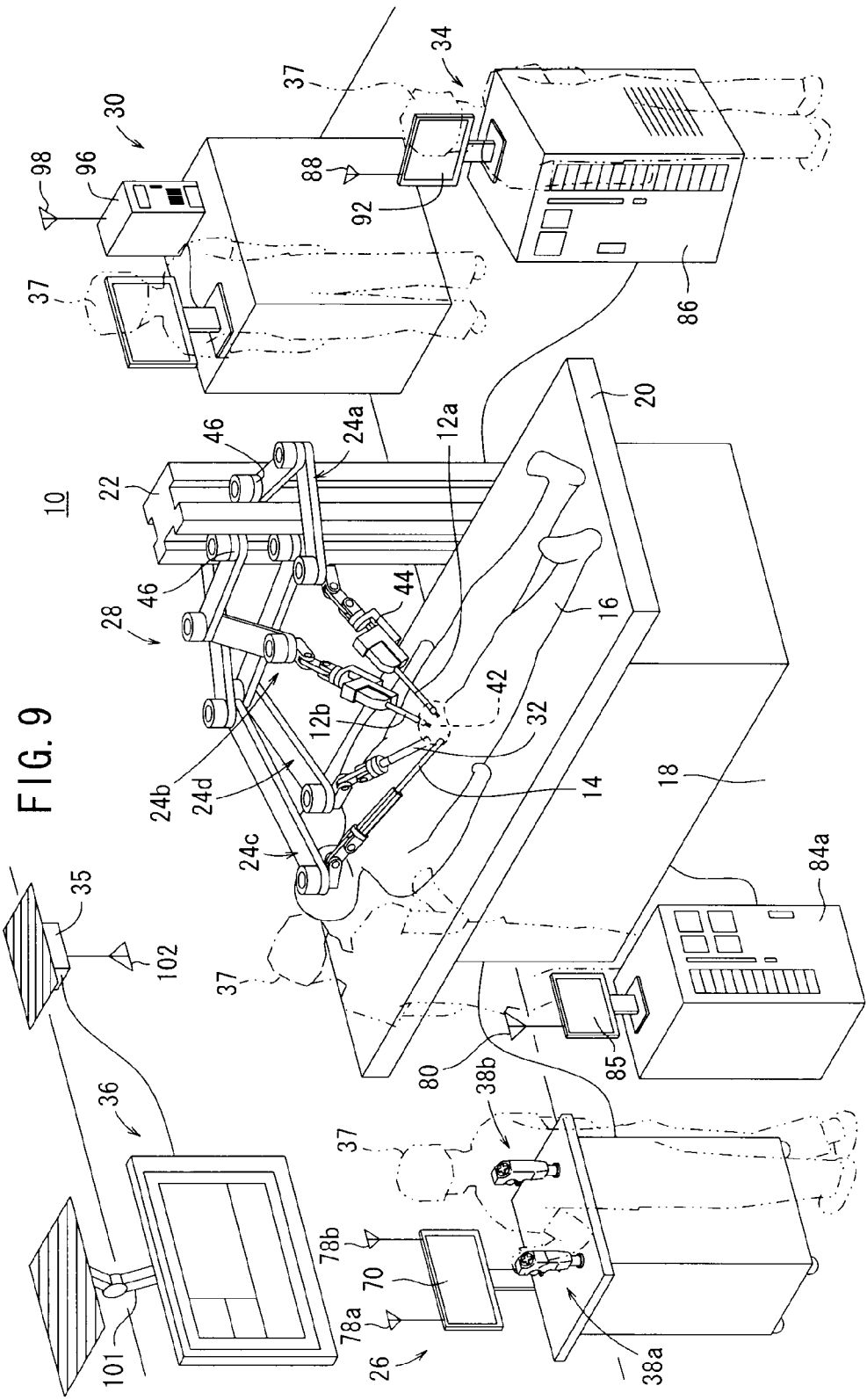
FIG. 9 is a perspective view of an operating room incorporating a surgical system according to a first modification of the invention.

FIG. 9 shows in perspective view an operating room incorporating a surgical system according to a first modification of the invention. In FIG. 9, the modified surgical system includes a separate housing 84a housing the transmitter 80 and the controller 82 therein, instead of the housing 84 which is attached to the distal end of the robot arm 24c together with a camera. The housing 84a is separate from the endoscope 14 on the robot arm 24c, so that the endoscope 14 on the robot arm 24c is simpler in structure. The housing 84a may support thereon a display monitor 85 for displaying an acquired endoscopic image. The surgical system 10 shown in FIG. 1 may also include an additional console similar to the separate housing 84a including the display monitor 85, in addition to the housing 84 on the proximal end of the endoscope 14.

The ultrasonic diagnostic device 34 generates an echo image (ultrasonic image) in response to a signal that is generated by the probe 32 on the distal end of the robot arm 24d. The ultrasonic diagnostic device 34 is of a nature that is in general use. As shown in FIG. 1, the ultrasonic diagnostic device 34 includes a housing 86 separate from the probe 32 on the robot arm 24d and housing therein a transceiver 88 connected to an antenna for transmitting information about the ultrasonic image to the wireless image processor 35 by way of wireless communications, and a controller 90 (see FIG. 7) for controlling the wireless communications or the like. The housing 86 may support thereon a display monitor 92 for displaying the acquired ultrasonic image. Alternatively, the transceiver 88 with the antenna may be mounted on the robot arm 24d as with the endoscope 14. The ultrasonic diagnostic device 34 is temporarily used when an echo image of the patient 16 needs to be acquired during the surgery.

The data server 30 is connected to a hospital network, for example. The data server 30 reads CT images and MRI images of the affected region of the patient 16 which were captured prior to the surgical operation performed by the surgical system 10, through the hospital network or a storage medium such as a memory card or the like, and stores the read images into a memory (affected region image storage) 94 (see FIG. 7). As shown in FIG. 1, the data server 30 has a housing 96 housing therein the memory 94, a transmitter 98 connected to an antenna for transmitting the image information (CT and MRI image data) of the affected region of the patient 16 which has been stored in the memory 94, to the wireless image processor 35 and the console 26 by way of wireless communications, and a controller 100 (see FIG. 7) for controlling the wireless communications or the like.

The surgical robot 28 which has the robot arms 24a through 24d and the console 26 is capable of measuring and controlling the positions of the distal ends of the manipulators 12a, 12b, e.g., the gripper positions on the distal-end working units 56, as coordinate points in a three-dimensional coordinate system, and capable of accurately and quickly moving the distal ends of the manipulators 12a, 12b in the three-dimensional coordinate system based on the measured coordinate positions.

Figure 6:
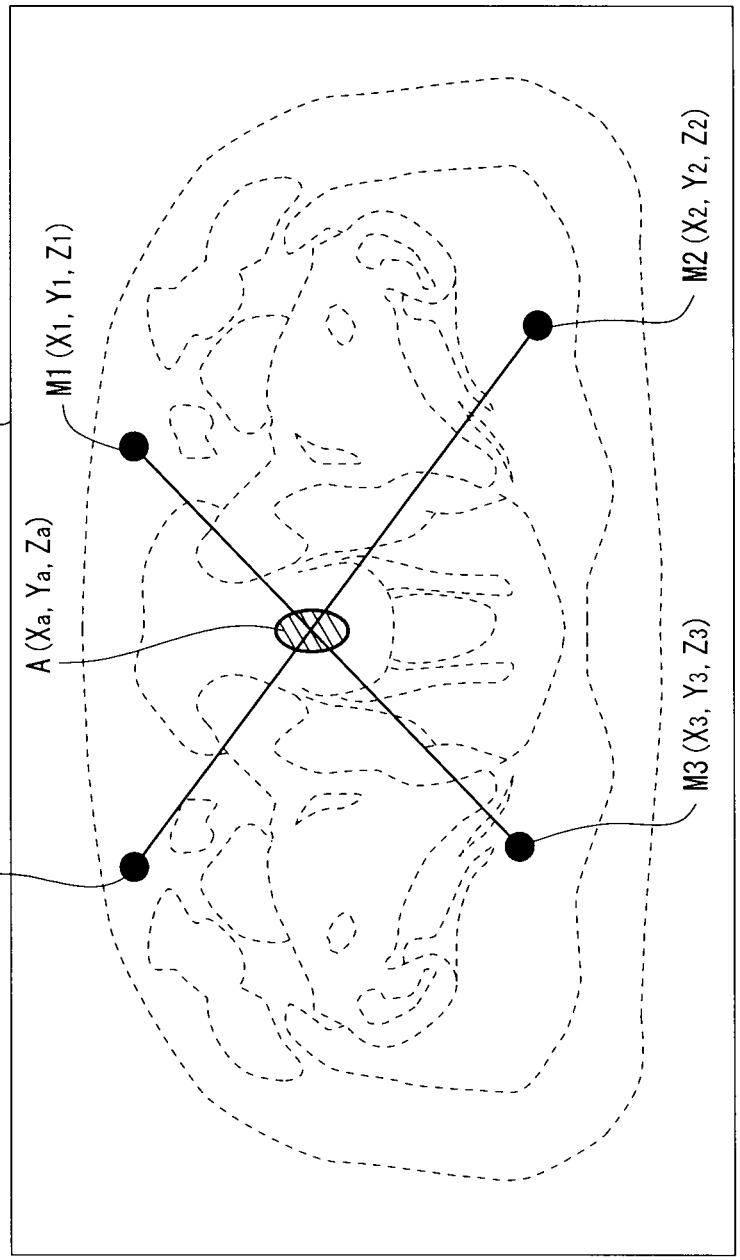
FIG. 6 is a diagram showing positional coordinates established in an X-ray CT image of an affected region of a patient.

Prior to the surgical operation to be performed by the surgical system 10, three-dimensional affected-region image information, i.e., CT image information and MRI image information, of the patient 16 which is stored in the data server 30 is transmitted from the transmitter 98 via the antenna 78b to the transceiver 78 of the console 26 by way of wireless communications (see FIG. 7). The three-dimensional affected-region image information of the patient 16 may alternatively be read into the console 26 through a wired link or from a recording medium. As shown in FIG. 6, the three-dimensional affected-region image information stored in the data server 30 includes three-dimensional coordinates (Xa, Ya, Za) of an affected region (cancer cells or the like) A and three-dimensional coordinates (X1, Y1, Z1) through (X4, Y4, Z4) of, three or more, e.g., four markers M1 through M4 around the affected region A that have been set on an affected-region image in a diagnostic image coordinate system.

The console 26 then converts the volume data of the coordinates (Xa, Ya, Za) of the affected region A and the coordinates (X1, Y1, Z1) through (X4, Y4, Z4) of the markers M1 through M4, which are data obtained from the data server 30 according to the diagnostic image coordinate system, into data according to an actual coordinate system of the surgical robot 28, i.e., a robot coordinate system. During the surgical operation, therefore, the positions of the distal ends of the manipulators 12a, 12b can easily and reliably be guided, i.e., navigated and assisted, based on the information about the coordinates of the affected region A and the markers M1 through M4. The coordinate information used to guide the manipulators 12a, 12b, i.e., used for surgical navigation, is transmitted from the console 26 to the wireless image processor 35 by way of wireless communications for display on the display unit 36 or the display monitor 70.

Figure 8:
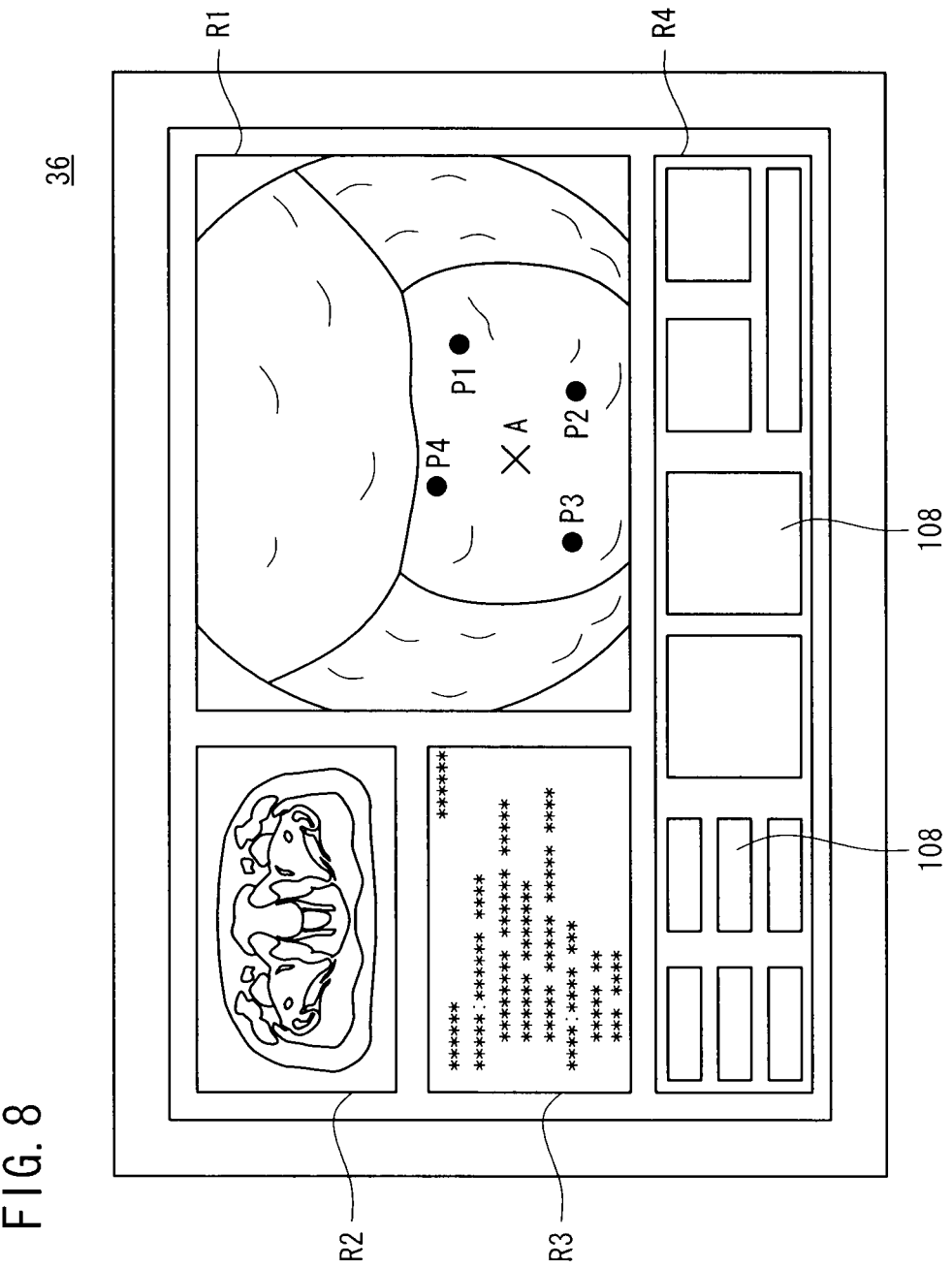
FIG. 8 is a view showing various items of information displayed on a display unit.

As shown in FIG. 8, predetermined manipulator position setting members P1 through P4 are placed in respective positions corresponding to the coordinate positions of the markers M1 through M4 around the affected region A of the patient 16 which are displayed on the display unit 36 or the display monitor 70. When the staff member 37 at the console 26 starts to perform a surgical technique on the patient 16, the staff member 37 brings the distal ends of the manipulators 12a, 12b successively into contact with the manipulator position setting members P1 through P4, whereupon the positions of the manipulators 12a, 12b are stored in a memory. The positional coordinates of the markers M1 through M4 in the diagnostic image coordinate system and the actual positional coordinates of the distal ends of the manipulators 12a, 12b in the actual coordinate system are now associated with each other by the console 26. The distal ends of the manipulators 12a, 12b can now be appropriately guided to the affected region A when the staff member 37 at the console 26 operates the joysticks 38a, 38b while seeing the display unit 36 or the display monitor 70. As described above, the surgical system 10 has a surgical navigation capability for guiding the manipulators 12a, 12b or the like based on the affected-region image (CT image or the like) of the patient 16 that has been captured.

FIG. 7 shows in block form a circuit arrangement of the surgical system 10.

As shown in FIG. 7, the wireless image processor 35 includes a transceiver 102 having an antenna for exchanging image information and operational information with the endoscope 14, the ultrasonic diagnostic device 34, the console 26, and the data server 30 by way of wireless communications, a processor 104 for controlling the transceiver 102 and processing information received by the transceiver 102 and information to be transmitted by the transceiver 102, and a multi-window processor (arithmetic unit, information processing means) 106 including the processor 104 as a function thereof, for controlling images to be displayed on the display unit 36 or the like.

The multi-window processor 106 can receive a plurality of items of information including a plurality of images from the endoscope 14 and the ultrasonic diagnostic device 34, system data from the console 26, and the like, process the received items of information, and output the processed items of information as signals to the display unit 36. The multi-window processor 106 can also control various many image display modes such as for dividing and combining displayed images and displaying various windows, in the display unit 36.

It is possible for the wireless image processor 35, i.e., the multi-window processor 106, to have a function for processing information about the surgical navigation, as is the case with the console 26.

The wireless communication capability of the surgical system 10 for transmitting various information may be of specifications capable of handling the amount of image information that is transmitted and received, and displaying moving images acquired by the endoscope 14 or the like on the display unit 36 without delay. For example, the wireless communication capability of the surgical system 10 may be provided by a high-speed communication scheme such as a wireless LAN, a UWB (Ultra-Wide-Band) link, or the like. The wireless LAN, for example, should preferably be a high-speed wireless LAN such as the one according to IEEE 802.11n or the like.

The display unit 36 comprises a large-size display unit for simultaneously displaying a plurality of items of information including images transmitted from the endoscope 14, the ultrasonic diagnostic device 34, the console 26, and the data server 30 and operational information of the surgical robot 28. For example, the display unit 36 comprises a liquid crystal display panel with touch-panel operation switches. The display unit 36 may alternatively comprise a plasma display panel, an EL display panel, or the like. When the staff member 37 at the console 26 operates the touch-panel operation switches 108 on the display unit 36 to enter an input signal, the input signal is transmitted through a control interface 110 of the wireless image processor 35 to the multi-window processor 106, which displays a desired image at a desired position in a desired size on the display unit 36 (see FIGS. 7 and 8). The display unit 36 may comprise a plurality of display units.

For example, the display unit 36 is supported on a universal arm 101 extending from the ceiling of the operating room 18 and hence can be placed in a desired position and oriented at a desired angle. However, the display unit 36 may alternatively be installed on the floor or hung on the wall.

Figure 12:
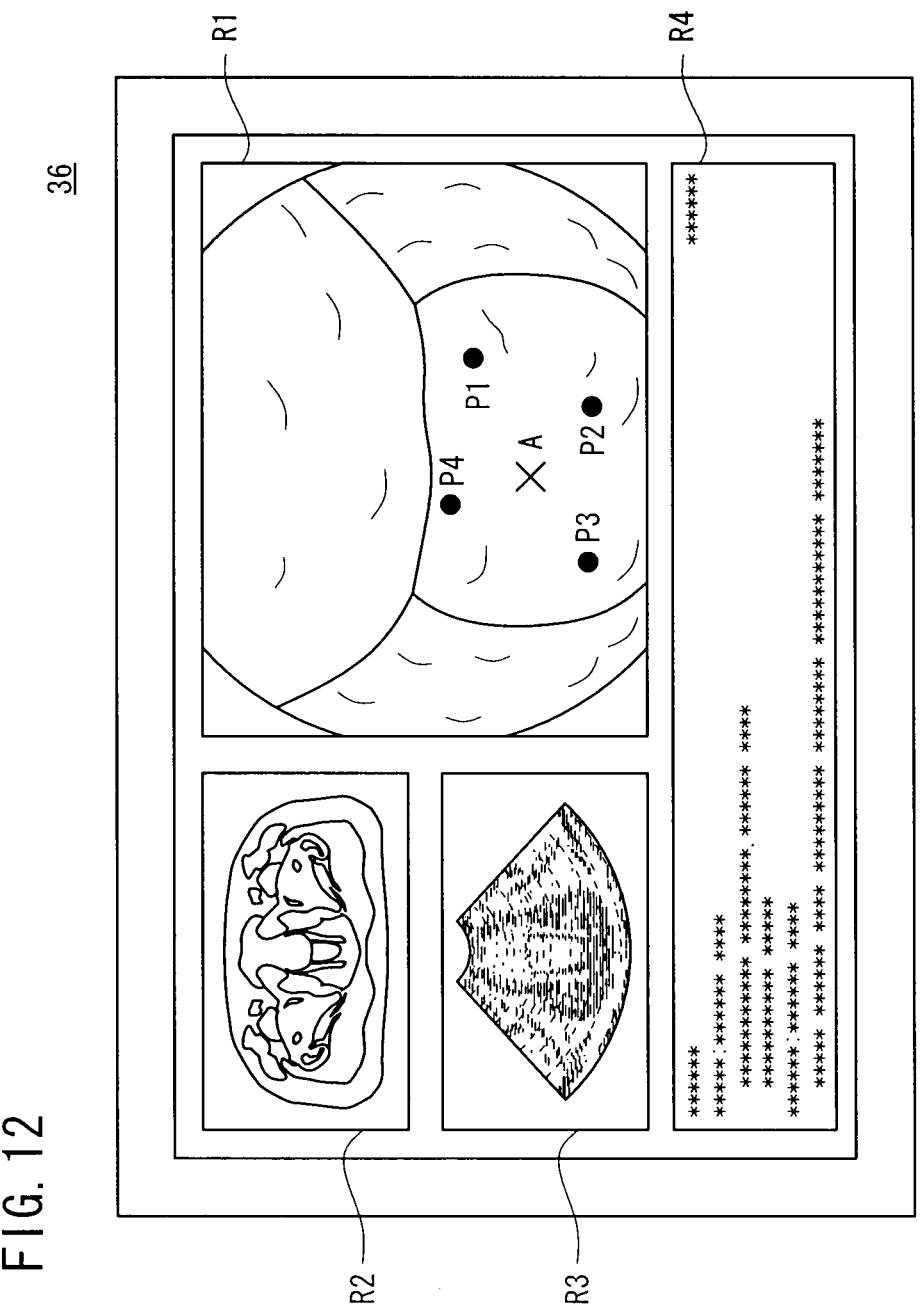
FIG. 12 is a view showing other items of information displayed on a display unit.

As shown in FIG. 8, the display unit 36 has a display screen divided into four areas R1 through R4 of different sizes. The largest area or window R1 displays an endoscopic image from the endoscope 14. The upper area or window R2, which is smaller than the area R1, displays an X-ray CT image from the data server 30. The area or window R3, which is positioned beneath the area R2, displays system data from the console 26. The lowest and wide area or window R4, which is positioned beneath the areas R1, R3, displays the touch-panel operation switches 108. For example, the area R3 may alternatively display an echo image (ultrasonic image) from the ultrasonic diagnostic device 34 (see FIG. 12). The system data from the console 26 represent the types of the manipulators mounted on the robot arms 24*a* through 24*d*, the types of the distal-end working units 56 (a gripper, scissors, an electrosurgical knife, and their specifications), usage histories of the manipulators, operational states (ON or OFF) of the manipulators, error information, warnings and their details, relative positional coordinates of the distal ends of the manipulators 12*a*, 12*b* with respect to the affected region A, the angle information of the distal-end working units 56 (the opening of the gripper 68, the angles of tilt around the pitch axis 64 and the yaw axis 66, the rotational angle around the roll axis), operational information (positional information) of the robot arms 24*a* through 24*d*, and the like. Consequently, the multi-window processor 106 has a function to process various information about endoscopic images, ultrasonic images, system data, etc., and setting a plurality of windows or areas, and simultaneously displaying the processed information in those windows or areas of the display unit 36.

Based on the processed information from the multi-window processor 106 and under the control of the multi-window processor 106, the display unit 36 displays, in the area R1, for example, an endoscopic image from the endoscope 14 and navigational data (coordinate information of the affected region A etc.) from the console 26 in a superposed fashion (see FIG. 8) for more effective surgical navigation. Specifically, diagnostic image data are transmitted as the navigational data from the data server 30 to the console 26 through the transmitter 98 and the antenna 78*b* by way of wireless communications. Then, information about the endoscopic image transmitted from the transmitter 80 to the console 26 through the transceiver 102, and the positional information of the affected region A based on the diagnostic image data are correlated to each other, i.e., superposed on each other, by the controller 79 of the console 26 or by another processor. The superposed information is then transmitted through the antenna 78*a* to the wireless image processor 35. Therefore, the endoscopic image and the navigation data (coordinate information etc. of the affected region A) can quickly be displayed in a superposed fashion on the display unit 36 (see FIG. 8). The above superposing process may be carried out by the wireless image processor 35, rather than the console 26.

The positions or areas for displaying the images on the display unit 36, the sizes of the displayed images, and the number of simultaneously displayed images may be changed by the staff member 37 using the touch-panel operation switches 108 under the control of the multi-window processor 106. For example, the staff member 37 may set the area R3 to display the system data from the data server 30 and the echo image from the ultrasonic diagnostic device 34 automatically alternately at predetermined time intervals. The display unit 36 may also display the conditions of the patient 16, including the blood pressure, the heart rate, etc., read from an instrument, not shown, connected to the patient 16.

All or some of the functions of the wireless image processor 35 may be incorporated in the display unit 36, and the wireless image processor 35 may be integrally combined with the display unit 36, rather than being separate from the display unit 36.

Operation of the surgical system 10 thus constructed will be described below.

First, a gas is introduced around the affected region of the patient 16 to form the body cavity 42, and the distal-end working units 56 and the joint shafts 54 of the manipulators 12*a*, 12*b* are inserted through the respective trocars 40 into the body cavity 42. The state in the body cavity 42 is confirmed on the display unit 36 or the display monitor 70 based on an endoscopic image captured by the endoscope 14 that has been inserted into the body cavity 42.

Then, the staff member (surgeon) 37 who handles the joysticks 38*a*, 38*b* operates the manipulators 12*a*, 12*b* on the distal ends of the robot arms 24*a*, 24*b* to perform a desired surgical technique while visually confirming the state in the body cavity 42 which is imaged by the endoscope 14.

Since the display unit 36 displays the navigation data from the console 26 in superposed relation to the endoscopic image from the endoscope 14 in the area R1 shown in FIG. 8, the staff member 37 who handles the joysticks 38*a*, 38*b* can appropriately perform the surgical technique.

As described above, the surgical system 10 according to the present embodiment includes the wireless communication means for exchanging information between multi-window processor 106 and the endoscope 14, the ultrasonic diagnostic device 34, the console 26, and the data server 30. Therefore, the display unit 36, which may be placed in any desired locations in the operating room 18 including the wall, the ceiling, and the floor, can simultaneously display a plurality of items of image information without the need for wires and cables in the operating room 18. The display unit 36 can even display image information from a device which is used only temporarily during the surgery, such as the ultrasonic diagnostic device 34, at the same time as the endoscopic image without the need for wires and cables in the operating room 18, for the staff member 37 to treat the patient 16 appropriately. Any instruments and devices other than the ultrasonic diagnostic device 34 may send image information to be displayed on the display unit 36 insofar as they have a transmitter for wireless communications, so that the patient 16 can be surgically treated more quickly and accurately. Inasmuch as the surgical system 10 has a greatly reduced number of wires and cables interconnecting the devices, the console 26, the ultrasonic diagnostic device 34, and other devices can be installed with greater freedom for layout.

The display unit 36 can easily be installed in or moved to a position which can be seen by all the staff members 37 including surgeons, nurses, technicians, etc. who are involved in the surgical operation performed by the surgical system 10. Consequently, all the staff members 37 can share various image information, operational information of the surgical robot 28, and the conditions of the patient 16, including the blood pressure, the heart rate, etc. which are displayed on the display unit 36. As the image information and other data are transmitted by way of wireless communications in the operating room 18, almost no wires and cables are exposed between the display unit 36, i.e., the wireless image processor 35, and the devices. The staff members 37 thus find it easy to move in the operating room 18, and can quickly prepare tools and instruments necessary for the surgery.

Figure 10:
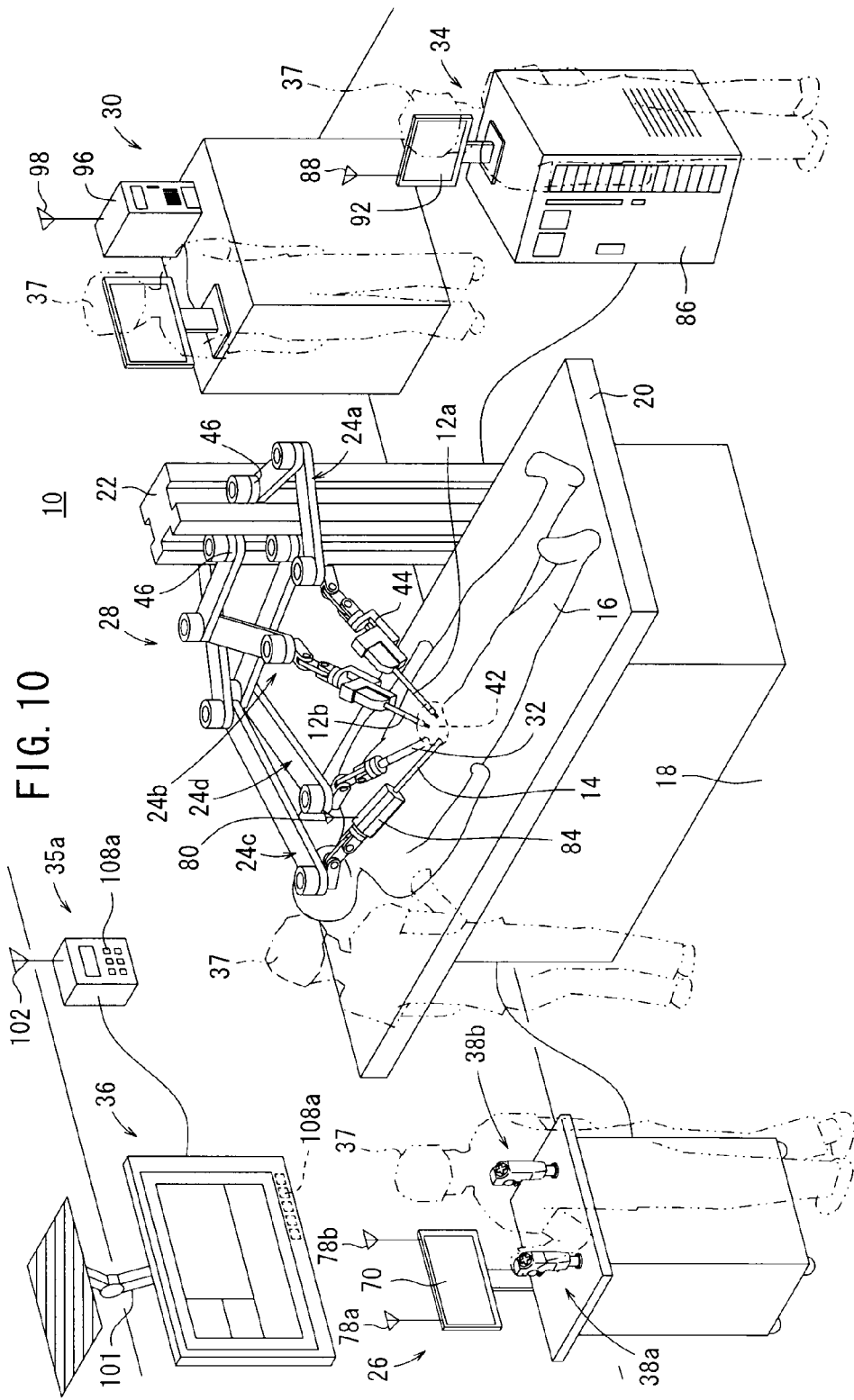
FIG. 10 is a perspective view of an operating room incorporating a surgical system according to a second modification of the invention.

As shown in FIG. 10, a surgical system 10 according to a second modification of the invention has a wireless image processor 35a with operation switches 108a, rather than the touch-panel operation switches 108 on the display unit 36.

Figure 11:
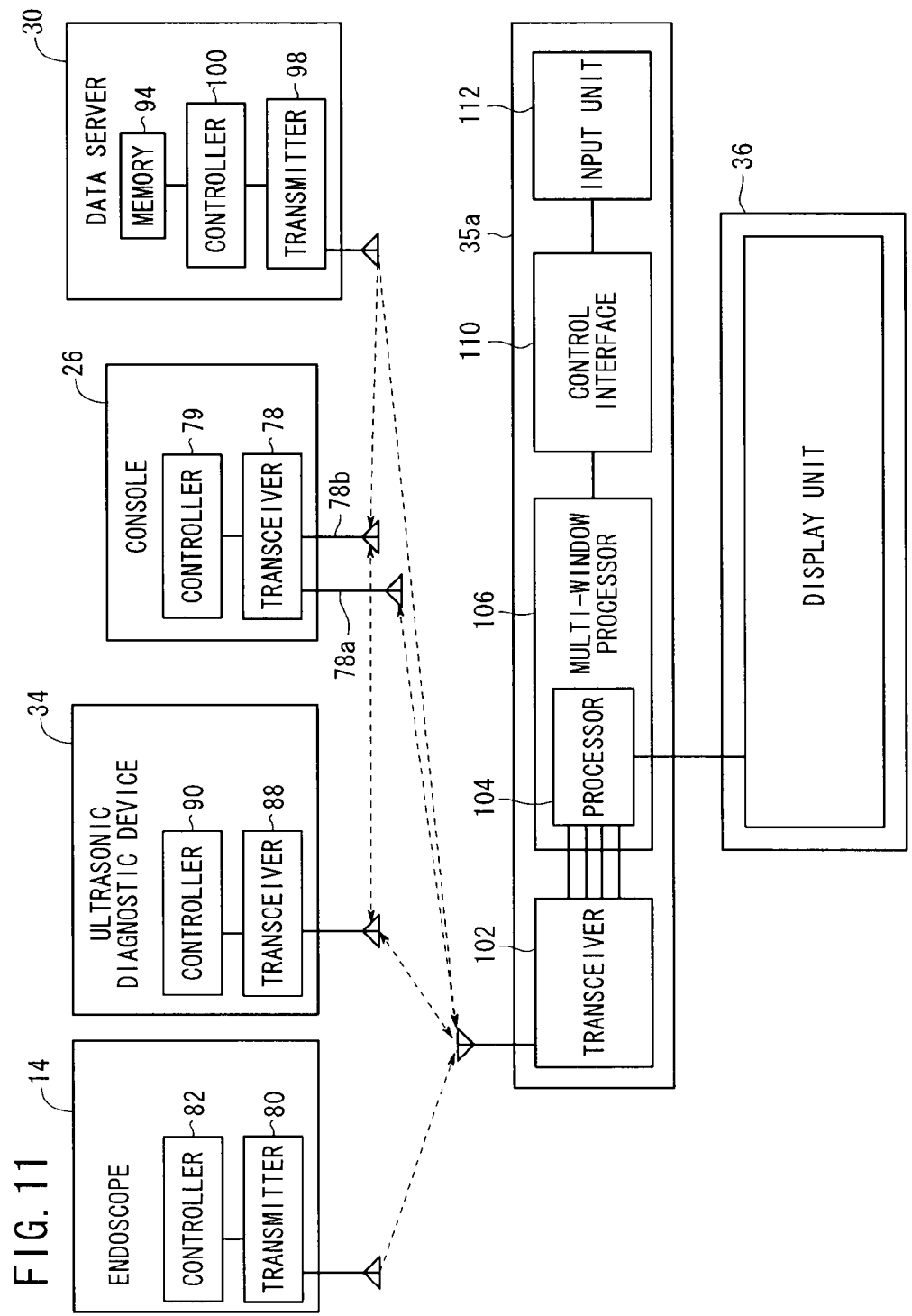
FIG. 11 is a block diagram of a circuit arrangement of the surgical system according to the second modification.

An operator, i.e., one of the staff members 37, operates the operation switches 108a of the wireless image processor 35a to set and change images displayed on the display unit 36. The wireless image processor 35a has an input unit 112 (see FIG. 11) for transmitting switch operation information to the control interface 110 in response to an input signal from the operation switches 108a. To make the operation switches 108a easily operable, the wireless image processor 35a should preferably be placed in a position that is easily accessible and does not present as an obstacle in the operating room 18, such as on the wall of the operating room 18.

Since the display unit 36 does not have touch-panel operation switches 108 on the display screen thereof, the display unit 36 can simultaneously display a greater number of items of information. For example, the display unit 36 can display an endoscopic image from the endoscope 14 in the area R1, an X-ray CT image from the data server 30 in the area R2, an echo image from the ultrasonic diagnostic device 34 in the area R3, and system data from the console 26 in the area R4 (see FIG. 12).

The operation switches 108a may instead be mounted on the outer frame of the display unit 36 as indicated by the broken lines in FIG. 10. The operation switches 108a should preferably comprise non-contact switches such as optical switches, switches triggerable on speech recognition, etc. The non-contact operation switches 108a allow the surgeon to change displayed images on the display unit 36 while the surgeon is performing the surgical operation on the patient 16.

The surgical system 10 may be a duplexed system for displaying at least endoscopic images from the endoscope 14 to guard against unexpected accidents.

Figure 13:
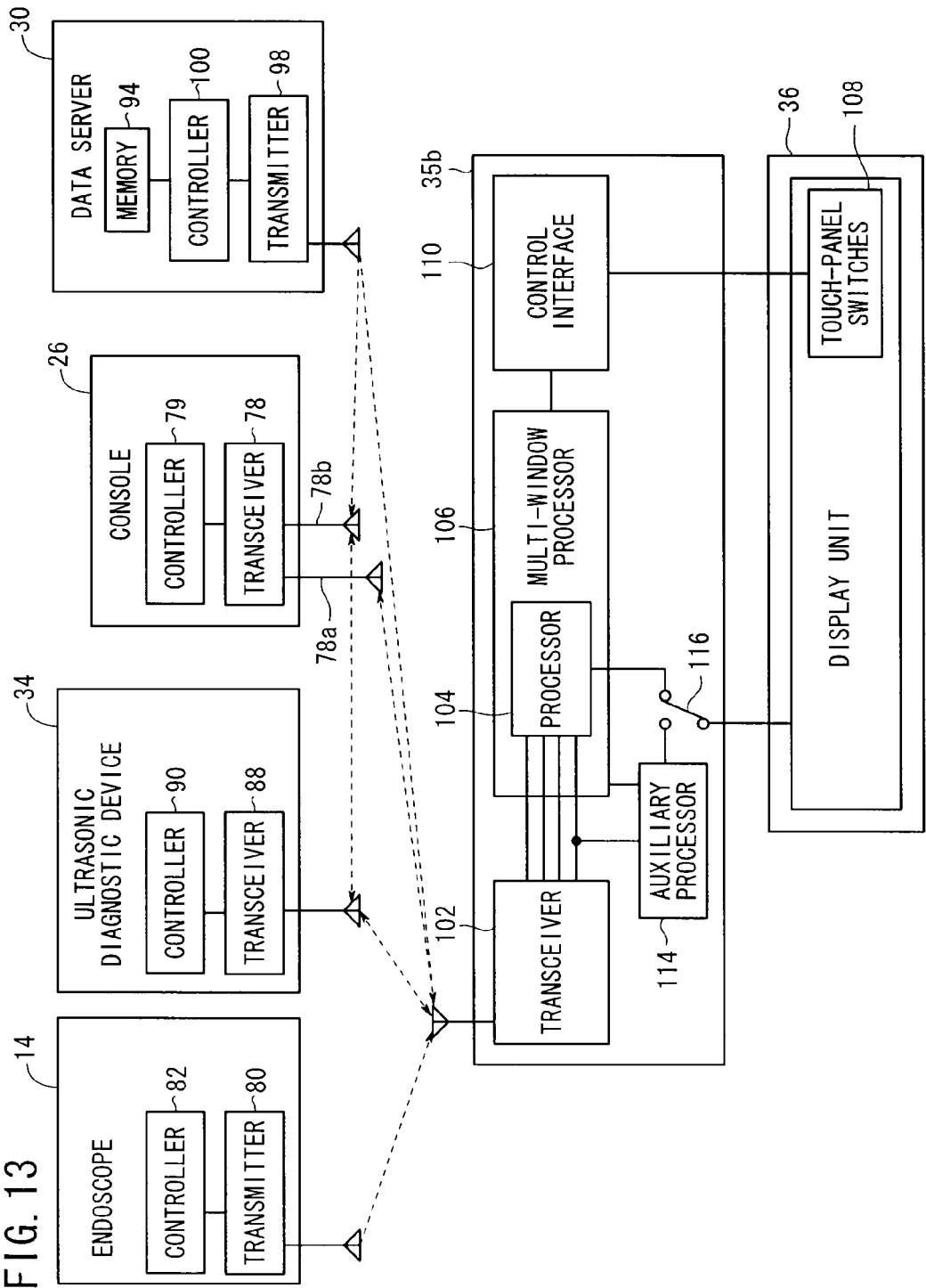
FIG. 13 is a block diagram of a circuit arrangement of a surgical system according to a third modification of the invention.

FIG. 13 is a block diagram of a circuit arrangement of a duplexed surgical system 10 according to a third modification of the invention. The duplexed surgical system 10 has a wireless image processor 35b including an auxiliary processor 114 for monitoring the operation of the multi-window processor 106 and a switch 116, instead of the wireless image processor 35. The auxiliary processor 114 has a function to process information about the endoscopic image transmitted from the endoscope 14 and displaying the image on the display unit 36, as with the processor 104, and serves as an information processing means for processing information to be displayed on the display unit 36, as with the multi-window processor 106 of the wireless image processor 35.

The transceiver 102 and the multi-window processor 106, i.e., the processor 104, are connected to each other by a plurality of signal lines. The auxiliary processor 114 interconnects one of those signal lines which transmits information about the endoscopic image from the endoscope 14, and the switch 116, and monitors the operation of the multi-window processor 106 based on fluctuations of the voltage of the multi-window processor 106 or the like. Normally, the switch 116 has its movable contact positioned to connect the processor 104 of the multi-window processor 106 to the display unit 36.

If the endoscopic image is no longer displayed on the display unit 36 due to an unexpected failure, then the auxiliary processor 114 serves as a bypass display means which shifts the movable contact of the switch 116 to a position connecting the auxiliary processor 114 to the display unit 36, and displays the endoscopic image on the display unit 36 by bypassing the multi-window processor 106. Therefore, the endoscopic image from the endoscope 14 is displayed on the display screen of the display unit 36 at all times without fail. The staff members 37 can thus continue performing the surgical technique on the patient 16 with the manipulators 12a, 12b without an interruption.

Figure 14:
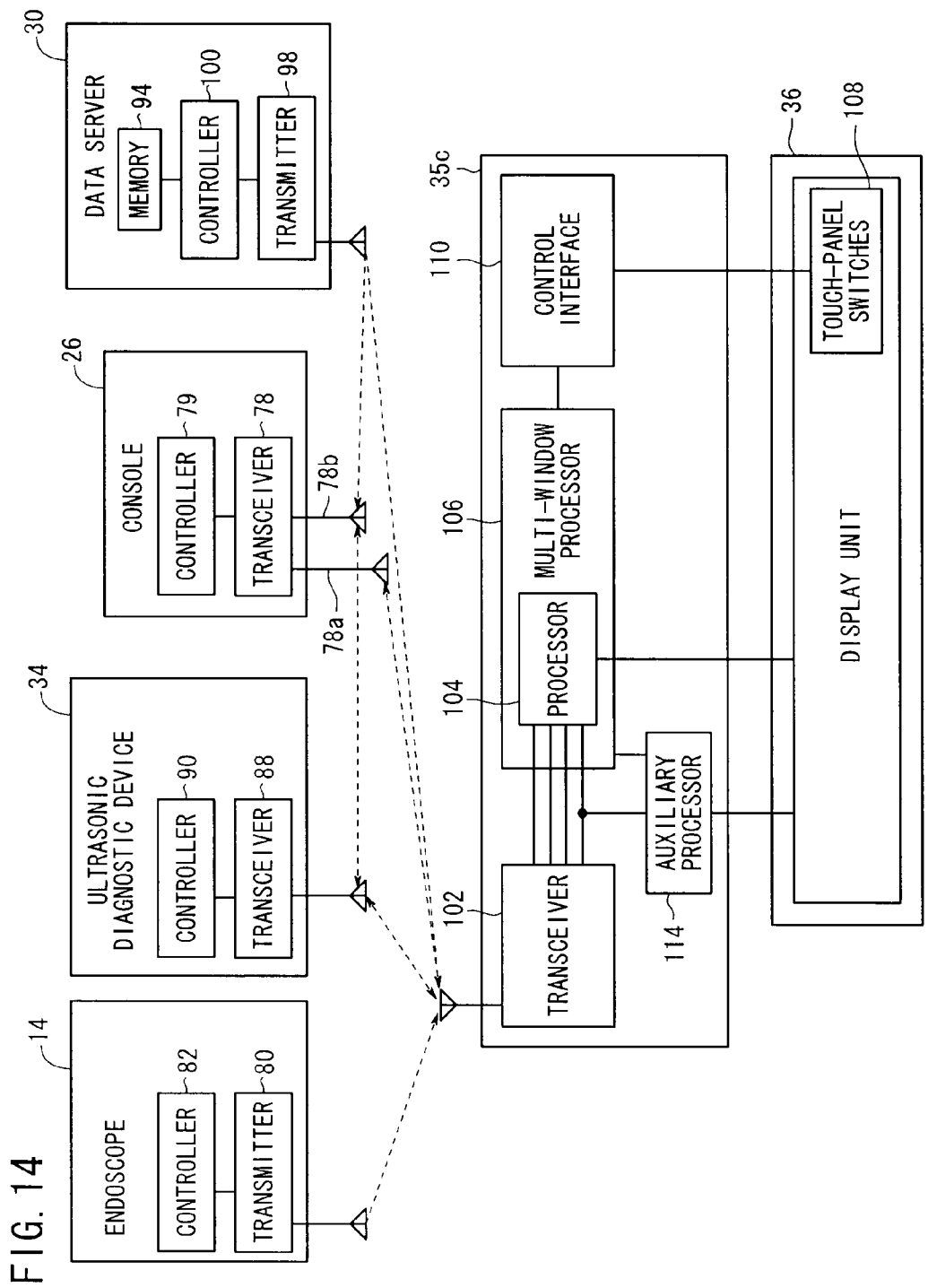
FIG. 14 is a block diagram of a circuit arrangement of a surgical system according to a fourth modification of the invention.

As shown in FIG. 14, a surgical system according to a fourth modification of the invention includes a wireless image processor 35c which is similar to the wireless image processor 35b shown in FIG. 13, except that it does not have the switch 116. Image information from the endoscope 14 is supplied from the multi-window processor 106 and the auxiliary processor 114 to the display unit 36 at all times. Normally, the display unit 36 displays an endoscopic image based on a signal from the multi-window processor 106 under the control of a controller, not shown, in the display unit 36 or the auxiliary processor 114 and the processor 104. When the multi-window processor 106 malfunctions, the display unit 36 displays an endoscopic image based on a signal from the auxiliary processor 114.

Figure 15:
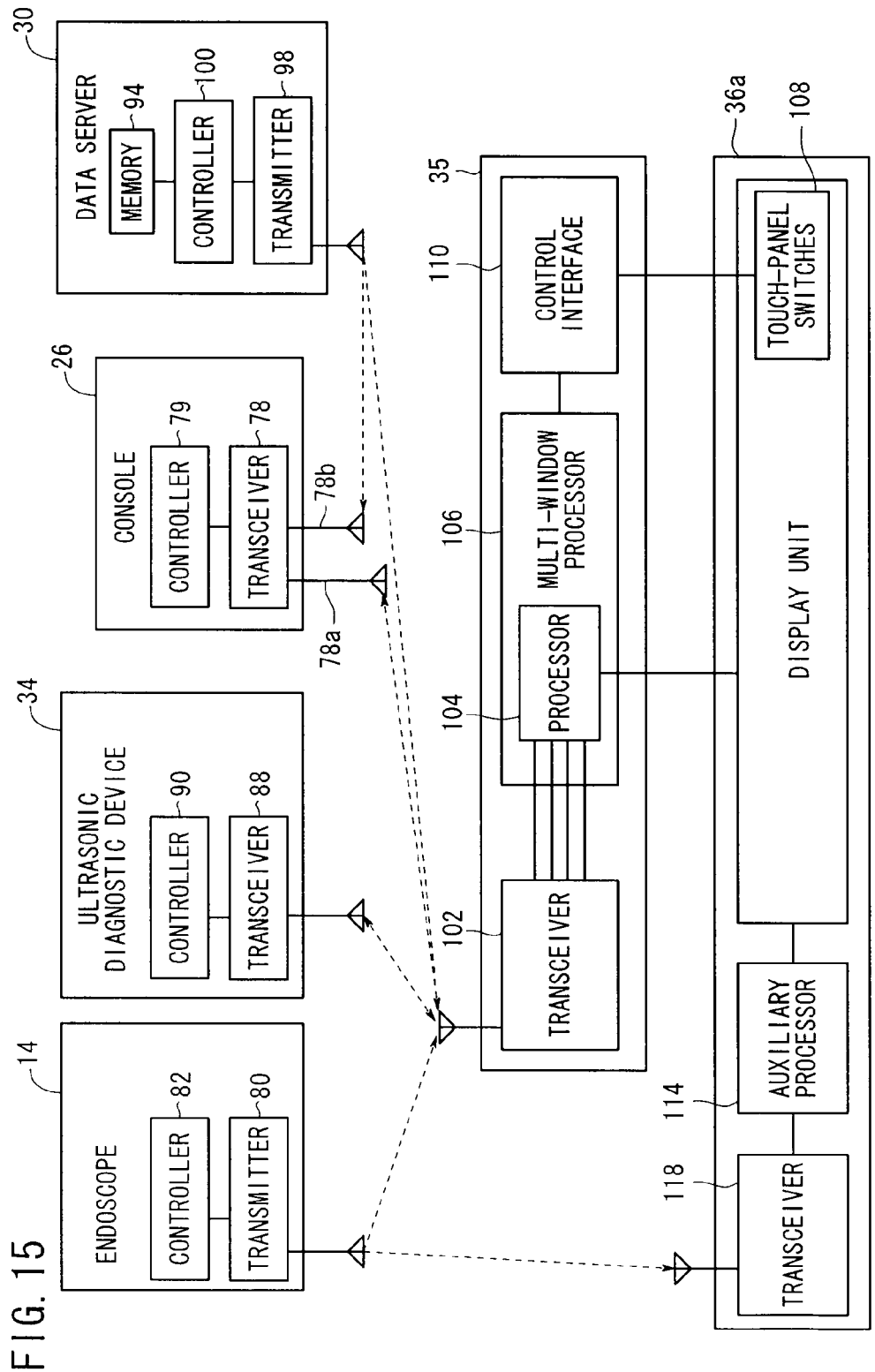
FIG. 15 is a block diagram of a circuit arrangement of a surgical system according to a fifth modification of the invention.

As shown in FIG. 15, a surgical system according to a fifth modification of the invention includes a display unit 36a having an auxiliary processor 114, instead of installing the auxiliary processor 114 in the wireless image processor 35b or the like. The display unit 36a also has a transceiver 118 having an antenna for receiving information about an endoscopic image from the endoscope 14 by way of wireless communications. The display unit 36a is capable of monitoring the operation of the multi-window processor 106. The auxiliary processor 114 may be replaced with a multi-window processor 106.

Figure 16:
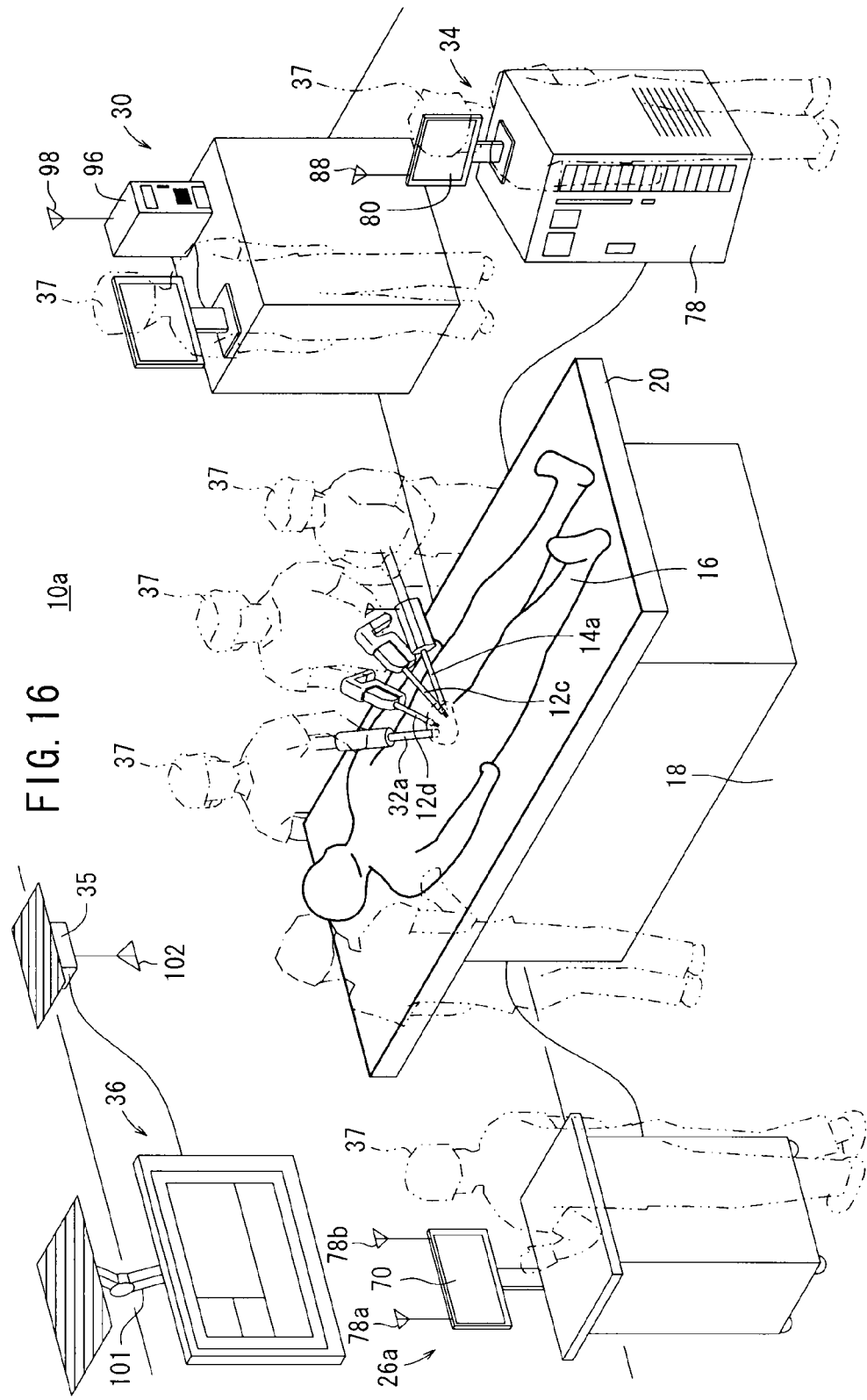
FIG. 16 is a block diagram of a circuit arrangement of a surgical system according to a sixth modification of the invention.

In the surgical systems 10 according to the above embodiments, the manipulators 12a, 12b, the endoscope 14, and the probe 32 are supported on and operated by the robot arms 24a through 24d of the surgical robot 28. In a surgical system 10a according to a sixth modification of the invention shown in FIG. 16, staff members 37 hold manipulators 12c, 12d, an endoscope 14a, and a probe 32a by hand, and a console 26a is free of the joysticks 38a, 38b.

Specifically, in the surgical system 10a, some of the staff members 37, who are surgeons, hold the manipulators 12c, 12d and perform a surgical technique using the manipulators 12c, 12d, and the other staff members 37 operate the endoscope 14a and the probe 32a, respectively. Of course, all or some of the manipulators 12c, 12d, the endoscope 14a, and the probe 32a may be operated by robot arms.

Figure 17:
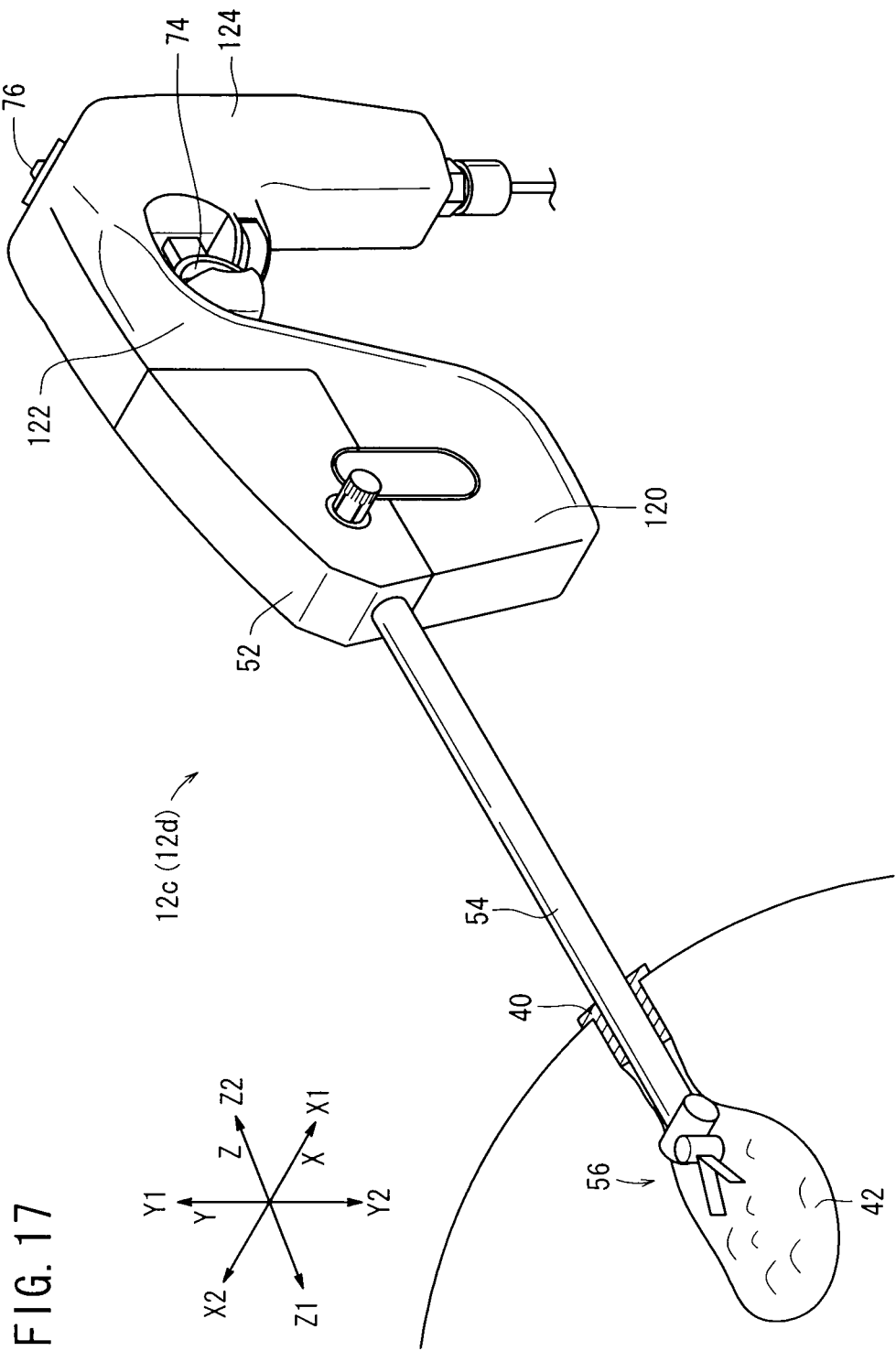
FIG. 17 is a perspective view of a manipulator used in the surgical system shown in FIG. 16.

As shown in FIG. 17, each of the manipulators 12c, 12d has an actuator block 120 on which the connecting block 52 is removably mounted. The connecting block 52 is disposed on the proximal end of the joint shaft 54 which supports the distal-end working unit 56 on its distal end. A grip handle 124 is connected by a bridge 122 to the end of the actuator block 120 which faces in the Z2 direction. The grip handle 124 extends from the end of the bridge 122 in the Y2 direction, and has a length large enough to be gripped by hand. A trigger lever 74 is disposed on a side of the bridge 122 which faces in the Y2 direction, and the composite input pad 76 is disposed on a slanted surface of the grip handle 124 which faces in the Y1 direction.

The surgical system 10a allows the staff members or surgeons 37 who handle the manipulators 12c, 12d and the other staff members 37 to share the current status of the surgical operation which is displayed on the display unit 36 for appropriate surgical treatments.

Each of the wireless image processors 35, 35a through 35c may be connected to a recorder 126, indicated by the broken lines in FIG. 7, for recording various information about endoscopic images from the endoscope 14 and images displayed on the display units 36, 36a. The recorder 126 may be connected to or separate from the wireless image processor 35, or may be connected to or separate from the display unit 36 or the like. The recorder 126 can store image data about surgical operations which may later be used for subsequent treatments or may later be played back to display immediately preceding images during surgical operations on demand.

The internal image capturing means may comprise an MRI system, an ultrasonic diagnostic device, or any apparatus capable of acquiring desired real-time internal images of the patient, rather than the endoscope.

Although certain preferred embodiments of the present invention have been shown and described in detail, it should be understood that various changes and modifications may be made therein without departing from the scope of the appended claims.

What is claimed is:

1. A surgical system for performing a surgical procedure on a patient, comprising:
    a manipulator performing the surgical procedure on the patient;
    internal image capturing means capturing an internal image of the patient;
    display means simultaneously displaying a plurality of items of information including said internal image captured by said internal image capturing means;
    information processing means transmitting said plurality of items of information to said display means and processing said plurality of items of information to be displayed by said display means;
    a medical robot system including
        a robot arm for moving said manipulator, said manipulator being mounted on said robot arm, said manipulator being operable by a driving source while being mounted on said robot arm,
        operating means for operating said manipulator and said robot arm, and
        operation control means controlling operation of said manipulator and said robot arm based on an input signal from said operating means; and
    a data server storing an affected-region image of an affected region of the patient and coordinate information about said affected-region image recorded in advance prior to performing the surgical procedure,
    wherein information about said internal image is transmitted from said internal image capturing means to said information processing means,
    wherein said affected-region image and said coordinate information about said affected-region image are transmitted from said data server to said information processing means,
    wherein said operation control means reads said coordinate information about said affected-region image stored in said data server, said coordinate information including positional coordinates of said affected region and positional coordinates of a plurality of markers in said affected-region image according to a diagnostic image coordinate system, and converting the positional coordinates of said affected region and of said markers into data according to a robot coordinate system of said robot arm to guide movement of said manipulator to said affected region based on said positional coordinates of said affected region and said positional coordinates of the markers,
    wherein said information processing means or said operation control means processes positional information of said affected region based on said positional coordinates of the affected region and said positional coordinates of said markers in correlation to the information about said internal image, and
    wherein said display means simultaneously displays said affected-region image, said internal image, and said positional information of said affected region in superposed relation to said internal image.

2. The surgical system according to claim 1, wherein operational information representing operating states of said manipulator and said robot arm is transmitted from said operation control means to said information processing means through a link including at least a portion based on wireless communications, and
    wherein said display means displays said operational information simultaneously with said internal image.

3. The surgical system according to claim 1, further comprising ultrasonic diagnostic means for acquiring an ultrasonic image of said affected region of the patient,
    wherein information about said ultrasonic image is transmitted from said ultrasonic diagnostic means to said information processing means through a link including at least a portion based on wireless communications, and
    said display means displays said ultrasonic image simultaneously with said internal image.

4. The surgical system according to claim 1, further comprising an operation switch for selecting and switching between said plurality of items of information displayed by said display means,
    wherein said operation switch is provided as a touch-panel switch on a display screen of said display means, or provided on said display means or on said information processing means.

5. The surgical system according to claim 1, wherein said information processing means includes a multi-window processor for setting and editing a plurality of windows on said display means for displaying said plurality of items of information simultaneously on said display means.

6. The surgical system according to claim 5, wherein said information processing means includes bypass display means for processing the information about the internal image and displaying the internal image on said display means by bypassing said multi-window processor.

7. The surgical system according to claim 1, wherein said display means displays system data including at least one of a type of the manipulator, a type of a distal-end working unit of the manipulator, and a usage history of the manipulator.

8. The surgical system according to claim 1, wherein said information processing means is connected to a recorder for recording endoscopic images or images displayed on the display means.

9. The surgical system according to claim 1, wherein the robot arm includes a slider attachment disposed on a distal end thereof, the slider attachment having at least one motor disposed therein to drive the manipulator.

10. The surgical system according to claim 9, wherein the slider attachment is slidable in a direction parallel to a longitudinal axis of the distal end of the robot arm via a slide mechanism.

11. The surgical system according to claim 9, wherein the manipulator includes a connecting block to removably mount to the slider attachment.

* * * * *